United States Patent [19]
Garret et al.

[11] Patent Number: 5,321,026
[45] Date of Patent: * Jun. 14, 1994

[54] PHENOTHIAZINE DERIVATIVES, THEIR PREPARATION AND PHARMACEUTICAL COMPOSITIONS CONTAINING THEM

[75] Inventors: Claude Garret, Fontenay sous Bois; Claude Guyon, Saint Maur des Fosses; Bernard Plau, Fresnes; Gerard Taurand, Creteil, all of France

[73] Assignee: Rhone-Poulenc Rorer S.A., France

[*] Notice: The portion of the term of this patent subsequent to Jan. 15, 2008 has been disclaimed.

[21] Appl. No.: 825,753

[22] Filed: Jan. 27, 1992

Related U.S. Application Data

[63] Continuation of Ser. No. 586,169, Sep. 21, 1990, abandoned.

[30] Foreign Application Priority Data

Sep. 21, 1989 [FR] France ................. 89 12403

[51] Int. Cl.$^5$ ................ C07D 279/28; C07D 417/06; A61K 31/54
[52] U.S. Cl. ............... 514/225.2; 514/225.5; 514/226.2; 544/41; 544/42; 544/46
[58] Field of Search ............. 544/41, 42, 46; 514/224.8, 225.2, 225.5, 226.2

[56] References Cited

U.S. PATENT DOCUMENTS

| | | | |
|---|---|---|---|
| 2,956,996 | 10/1960 | Craig et al. | 544/41 |
| 3,112,310 | 11/1963 | Cusic et al. | 544/42 |
| 4,912,105 | 3/1990 | Garret et al. | 544/42 |
| 4,985,419 | 1/1991 | Garret et al. | 544/41 |
| 5,049,669 | 9/1991 | Garret et al. | 514/226.2 |

FOREIGN PATENT DOCUMENTS 860330 2/1961 United Kingdom ............ 544/41

OTHER PUBLICATIONS

"Opioid Binding Sites of the K-Type in Guinea-Pig Cerebellum" by L. E. Robson, et al. *Neuroscience* (1984) vol. 12, No. 2, pp. 621–627.

"The Action of Morphine and Related Substances on Contraction and on Acetylcholine Output of Coazially Stimulated Guinea-Pig Ileum" by W. D. M. Paton, *Brit. J. Pharmacol.* (1957), pp. 119–127.

"A Method for Determining Loss of Pain Sensation" by Fred E. D'Amour, et al., *J. Pharmacology* vol. 72, (1941), pp. 74–79.

*Primary Examiner*—Mukund J. Shah
*Assistant Examiner*—Philip I. Datlow
*Attorney, Agent, or Firm*—Morgan & Finnegan

[57] ABSTRACT

New phenothiazine derivatives of general formula (I) in which

R represents 4- to 6-membered cycloalkyl, or represents —CH$_2$R" in which R" is hydrogen, alkyl containing 1 to 5 carbon atoms, alkenyl or alkynyl containing 2 to 4 carbon atoms, cycloalkyl (3- to 6-membered), phenyl, optionally substituted (with 1 or 2 halogen atoms or with a hydroxyl, alkyl, alkyloxy, trifluoromethyl or nitro radical) or heterocyclic selected from furyl, thienyl or pyridyl, and R' either represents a radical of general formula (IIa) in which R$_1$ and R$_2$, which may be identical or different, are alkyl, cycloalkylalkyl, hydroxyalkyl or acetyloxyalkyl or, together with the nitrogen atom to which they are attached, form a saturated or partially unsaturated 4- to 7-membered heterocycle optionally substituted with 1 or 2 alkyl, hydroxyalkyl or acetyloxyalkyl radicals, and R$_3$ is phenethyl or alkyl optionally substituted with cycloalkyl (3 to 6 carbons) or benzoyl, or represents a radical of general formula (IIb) in which R$_1$ and R$_2$ are defined as above.

The new products are useful as antispasmodics.

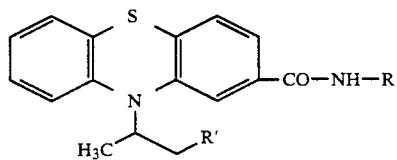

(I)

(Abstract continued on next page.)

-continued
(IIa)
-continued
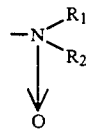
(IIb)
8 Claims, No Drawings

PHENOTHIAZINE DERIVATIVES, THEIR PREPARATION AND PHARMACEUTICAL COMPOSITIONS CONTAINING THEM

This is a continuation of application Ser. No. 07/586,169, filed on Sep. 21, 1990, now abandoned.

FIELD OF THE INVENTION

The present invention relates to new phenothiazine derivatives of general formula:

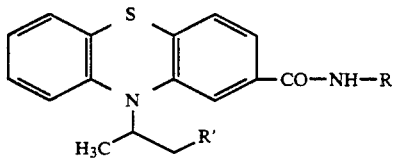

to their preparation and to pharmaceutical compositions containing them.

BACKGROUND OF THE INVENTION

In the phenothiazine field, many products have been demonstrated, especially for their activity with respect to the central nervous system, in particular amides derived from phenothiazine, of general formula:

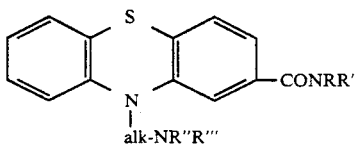

in which R is, in particular, a hydrogen atom, have been described in U.S. Pat. No. 3,112,310. Thioamides derived from phenothiazine, of general formula:

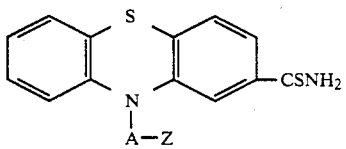

in which A is a carbon-containing chain and Z is, in particular, a dialkylamino radical or a nitrogenous heterocycle, have also been described in Belgian Patent No. 612,885.

DETAILED DESCRIPTION OF THE INVENTION

It has now been found that the products derived from phenothiazine of general formula (I), which possess a preferential affinity for kappa type opiate receptors while manifesting little or no central action in vivo, are especially advantageous, in particular in the antispasmodic field.

In the general formula (I)

the symbol R represents a 4- to 6-membered cycloalkyl radical or represents a radical —CH$_2$R″, in which R″ is a hydrogen atom, an alkyl radical containing 1 to 5 carbon atoms, an alkenyl or alkynyl radical containing 2 to 4 carbon atoms, a 3- to 6-membered cycloalkyl radical, a phenyl radical, optionally substituted (with 1 or 2 halogen atoms or with a hydroxyl, alkyl, alkyloxy, trifluoromethyl or nitro radical), or a heterocyclic radical selected from furyl, thienyl or pyridyl, and the symbol R' represents: either a radical of general formula

in which the symbols R$_1$ and R$_2$, which may be identical or different, represent alkyl, cycloalkylalkyl, hydroxyalkyl or acetyloxyalkyl radicals, or together with the nitrogen atom to which they are attached, form a saturated or partially unsaturated 4-to 7-membered heterocycle optionally substituted with 1 or 2 alkyl, hydroxyalkyl or acetyloxyalkyl radicals, and the symbol R$_3$ represents a phenethyl radical or an alkyl radical optionally substituted with a cycloalkyl radical containing 3 to 6 carbon atoms or benzoyl radical, or a radical of general formula:

in which R$_1$ and R$_2$ are defined as above.

It is understood that (except where otherwise stated) the alkyl radicals mentioned above are linear or branched and contain 1 to 4 carbon atoms. By way of example, the 4- to 7-membered heterocycle mentioned above can be chosen from: pyrrolidinyl, piperidinyl or perhydroazepinyl.

The products of general formula (I) exist in isomeric forms; it is understood that the products of the L form as well as the mixtures of isomeric forms lie within the scope of the present invention.

According to the invention, the phenothiazine derivatives of general formula (I) for which R' is a radical (IIa) may be obtained from a phenothiazine derivative of general formula:

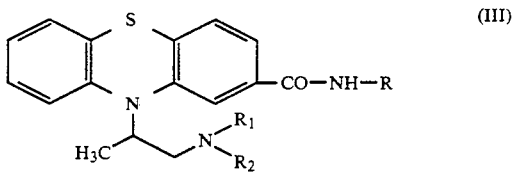

in which R, R$_1$ and R$_2$ are defined as above, by the action of a product of general formula:

in which R$_3$ is defined as above and X represents a halogen atom selected from chlorine, bromine or iodine, or a sulphate or alkylsulphonyloxy radical or a phenylsulphonyloxy radical in which the phenyl radical is optionally substituted with one or more halogen atoms or alkyl or nitro radicals.

The reaction is generally performed in an organic solvent such as an amide (e.g. dimethylformamide, hexamethylphosphorotriamide, dimethylacetamide), a nitrile (e.g. acetonitrile), a ketone (e.g. acetone), a nitro derivative (e.g. nitromethane or nitrobenzene), N-methylpyrrolidone or a mixture of these solvents, at a temperature between 0° C. and the refluxing temperature of the reaction mixture. The reaction is optionally performed in the presence of an alkali metal salt (e.g. sodium carbonate or potassium carbonate).

The phenothiazine derivatives of general formula (III) may be obtained from a phenothiazine derivative of general formula:

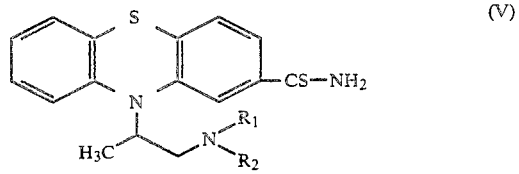

in which $R_1$ and $R_2$ are defined as above, by the action of an amine of general formula:

in which R is defined as above, and then, where appropriate, if the intermediate substituted thioamide has been isolated, this thioamide is oxidized to the corresponding amide.

The reaction is advantageously performed in an organic solvent such as an alcohol (e.g. ethanol, methanol, isopropanol) or without a solvent, at a temperature of between 100° and 250° C. It is sometimes advantageous to work in the presence of hydrogen sulfide.

In practice, to prepare the amide of general formula (III), it is not essential to isolate the intermediate substituted thioamide. When it is desired to isolate the amide of general formula (III) directly, without prior isolation of the intermediate thioamide, chromatography or crystallization is employed.

Where appropriate, the oxidation of the intermediate thioamide to the corresponding amide is advantageously performed by means of a mercuric salt (e.g. mercuric acetate) or a cuprous salt, in an organic solvent such as ketone (e.g. acetone), an alcohol, an ester or a carboxylic acid such as, e.g. acetic acid, at a temperature of between 0° and 100° C.

It is possible to perform the oxidation using procedures analogous to the methods described by:
H. J. Kim et al., Synthesis, 11, 970 (1986),
M. T. M. El-Wassimy, Tetrahedron 39 (10), 1729 (1983),
K. A. Jergenson et al, Tetrahedron 38 (9), 1163 (1982),
A. G. Samuelson et al., Tetrahedron Letters, 27 (33), 3911 (1986).

The amides of general formula (III) may also be obtained from an acid of general formula:

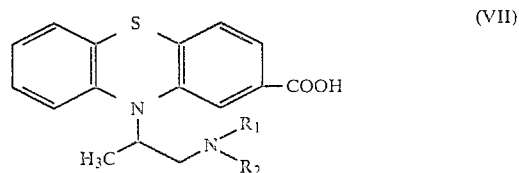

in which $R_1$ and $R_2$ are defined as above, by any known method for obtaining a substituted amide from an acid without affecting the remainder of the molecule.

The conversion is performed, in particular, by the action of an amide of general formula (VI) on a reactive derivative of the acid, optionally prepared in situ, e.g. the acid chloride, an activated ester or a mixed anhydride, in an organic solvent such as an ether or a chlorinated solvent (e.g. methylene chloride, chloroform, dichloroethane) or in an amide (dimethylformamide), in the presence of an acceptor for acid such as a nitrogenous organic base such as, e.g., a trialkylamine (in particular triethylamine), at a temperature of between −40° and +40° C.

It is also possible to react the amine of general formula (VI) directly with the acid by working in the presence of a condensing agent such as carbodiimide (dicyclohexylcarbodiimide), N, N'-carbonyldiimidazole or N-hydroxybenzotriazole, in an organic solvent as mentioned above, and at a temperature as defined above.

It is understood that, in cases where the radical R of the amine of general formula (VI) contains functions capable of interfering with the reaction, the radical must be protected beforehand. The protective radical introduced is removed subsequent to the reaction. In particular, when the radical R contains a hydroxyl radical, it is preferable to protect this radical. The protection is accomplished, e.g. in the form of a methoxy or benzyloxy radical, which can be removed, respectively, by treatment with hydrobromic acid or boron tribromide, or by hydrogenolysis in the case of the benzyloxy radical.

The phenothiazine derivative of general formula (V) may be obtained from a nitrile of general formula:

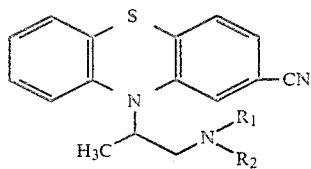

in which $R_1$ and $R_2$ are defined as above, by any known method for obtaining a thioamide from a nitrile without affecting the remainder of the molecule.

The reaction is generally performed in an anhydrous basic medium, in the presence of hydrogen sulfide, at a temperature of between 0° and 100° C. The reaction is advantageously performed in the presence of a nitrogenous organic base such as triethylamine, in an organic solvent such as pyridine.

The acid of general formula (VII) may be obtained from a nitrile of general formula (VIII) by any known method for obtaining an acid from a nitrile without affecting the remainder of the molecule. The conversion is performed, in particular, by hydrolysis in an acidic or basic medium in an organic solvent at a temperature between 50° C. and the refluxing temperature of the reaction mixture. The reaction is advantageously performed in glycol in the presence of potassium hydroxide.

The nitrile of general formula (VIII) may be obtained in accordance with the following scheme:

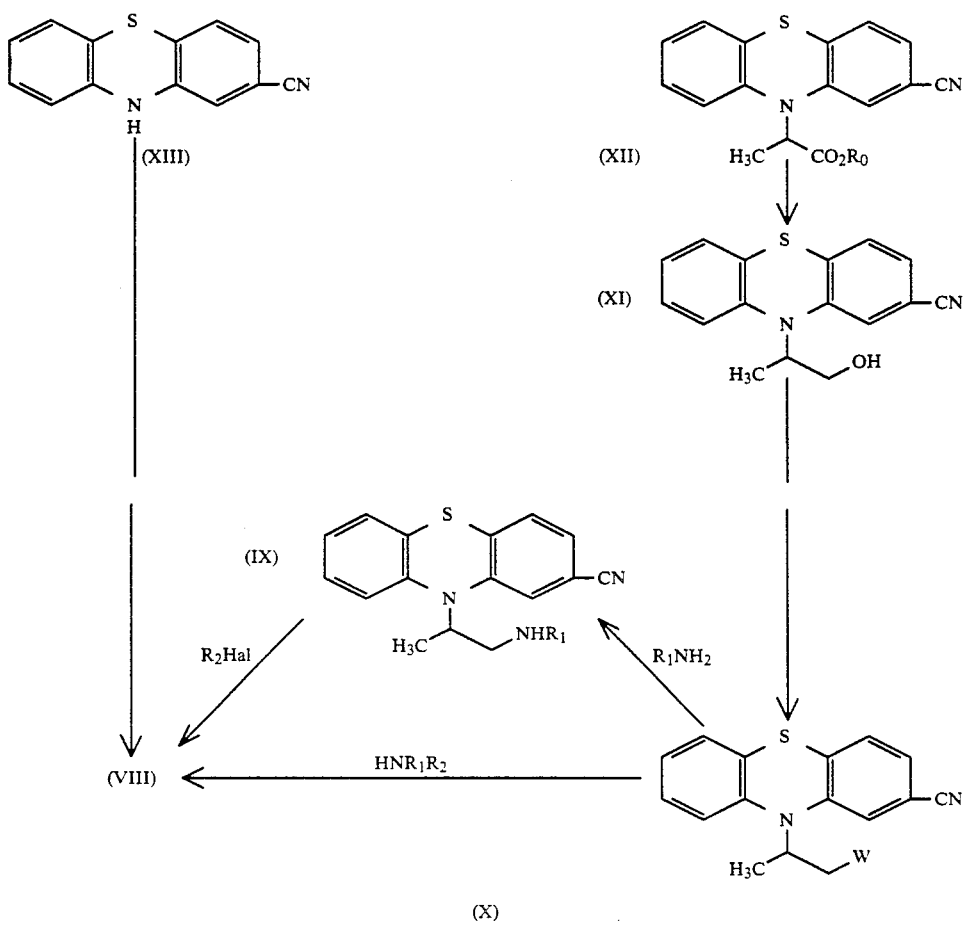

in which W is a halogen atom or a p-toluene-sulphonyloxy, methylsulphonyloxy or diaryloxyphosphoryloxy residue and $R_0$ is an alkyl radical containing 1 to 4 carbon atoms (e.g. ethyl), and for which the working conditions are defined in greater detail below in the examples.

The nitrile of general formula (XIII) may be obtained as described in U.S. Pat. No. 2,877,224.

According to the invention, the products of general formula (I) for which R' is a radical (IIa) may also be obtained from a phenothiazine derivative of general formula:

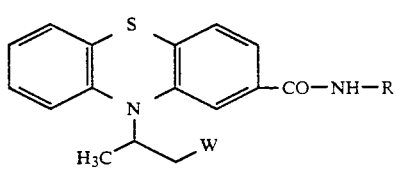

(XIV)

in which R and W are as defined above, by the action of a tertiary amine of general formula:

(XV)

in which $R_1$, $R_2$ and $R_3$ are defined as above.

The reaction is generally performed in an organic solvent, e.g. in a solvent as mentioned above for the reaction of a product of general formula (III) with a product of general formula (IV), at a temperature between 0° C. and the refluxing temperature of the reaction mixture.

The products of general formula (XIV) may be obtained in a manner analogous to the preparation of the products of general formula (I), according to the following scheme:

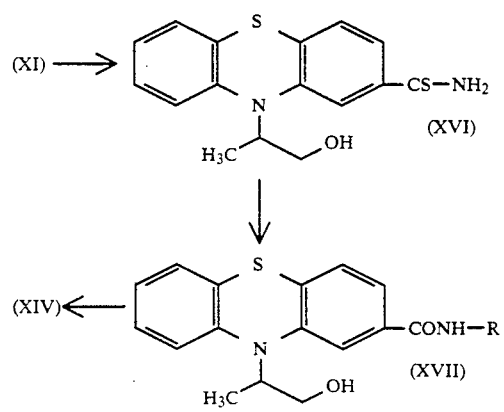

According to the invention, the phenothiazine derivatives of general formula (I) for which R' is a radical (IIb) may be obtained from a phenothiazine derivative of general formula (III) by any known method for obtaining an N-oxide from the corresponding amine without affecting the remainder of the molecule.

The conversion is advantageously performed by oxidation with hydrogen peroxide, in an organic solvent such as ethanol, at a temperature of between 0° and 50° C.

The isomers of the products of general formula (I) may be obtained according to known methods.

The procedure is accomplished, in particular, by preparation of the isomer of the phenothiazine derivative of general formula (XI), which is then converted to phenothiazine derivative of general formula (I) by the methods described above.

The optically active derivative of the product of general formula (XI) is, in particular, obtained by preparation of the ester of a diacid, formation of an optically active salt, separation of the isomers by crystallization and saponification of the isomer obtained.

More especially, the ester is obtained by means of the anhydride of a diacid such as, e.g., phthalic anhydride or maleic or succinic anhydride. The salt is formed by the addition of an optically active amine, for example (+)-1-phenylethylamine or (−)-1-phenylethylamine.

In the examples which follow, the phenothiazine derivatives prepared from the alcohol of general formula (XI) for which the optical rotation in solution in chloroform is negative are referred to as the L series.

The products of general formula (I) may be purified by chromatography or crystallization.

According to the invention, the phenothiazine derivatives of general formula (I) for which R' is a radical (IIa) are obtained in the state of quaternary ammonium salts whose nature is dependent on the derivative $R_3X$ selected for their preparation or on the radical W of the derivative of general formula (XIV). It is understood that the salts obtained may be converted, where appropriate, to other pharmaceutically acceptable salts, according to the usual methods.

As pharmaceutically acceptable salts, the addition of salts with inorganic acids, such as chlorides, bromides, sulphates, nitrates and phosphates, or organic acids, such as acetates, propionates, succinates, maleates, fumarates, methanesulphonates, p-toluenesulphonates, isethionates or substitution derivatives of these compounds, may be mentioned.

The phenothiazine derivatives of general formula (I) exhibit an especially advantageous antispasmodic activity as the result of their preferential affinity for kappa receptors, their weak or non-existent central action and their low toxicity.

They were, in effect, shown to be active at concentrations of between 10 and 500 nM in the binding method employing tritiated ethylketocyclazocine in in guinea pig cerebellum homogenates, based on the technique of L.E. Robson et al., Opioid binding sites of the kappa type in guinea pig cerebellum, Neuroscience, 12, 621 (1984).

They were also shown to be active in the technique of inhibition of contractions induced by electrical stimulation on isolated guinea pig ileum (based on the technique of W.D.M. Paton, Brit. J. Pharmacol., 11, 119 (1957)) at concentrations of between 5 and 300 nM.

Moreover, the products according to the invention posses little or no central action. In effect, their active dose was shown to be either in the region of 10 mg/kg s.c. or more than 30 mg/kg s.c. in mice in the method described by d'Amour and Smith, J. Pharmacol., 72, 74 (1941).

Finally, the acute toxicity ($LD_{50}$) of the products of general formula (I) in mice is low at the doses at which they are used. Their $LD_{50}$ amounts to approximately 60 mg/kg p.o., or more generally doses markedly larger than 100 mg/kg p.o.

Of special importance are the products of general formula (I) in which
  the symbol R represents a radical —$CH_2R''$ in which R'' is an alkyl radical containing 1 to 5 carbon atoms, an alkenyl or alkynyl radical containing 2 to 4 carbon atoms, a 3- to 6-membered cycloalkyl radical or a phenyl radical optionally substituted with an alkyl radical, and
  the symbol R' represents: either a radical of general formula (IIa) in which the symbols $R_1$ and $R_2$, which may be identical or different, represent alkyl radicals or, together with the nitrogen atom to which they are attached, form a saturated or partially unsaturated 4- to 7-membered heterocycle and the symbol $R_3$ represents a phenethyl radical or an alkyl radical optionally substituted with a cycloalkyl radical containing 3 to 6 carbon atoms or benzoyl radical, or a radical of general formula (IIb).

And among these products, more especially important are the products of general formula (I) in which:
  the symbol R represents a radical —$CH_2R''$ in which R'' is an alkyl radical containing 2 to 4 carbon atoms, an alkenyl radical containing 2 to 4 carbon atoms, a 3- or 4-membered cycloalkyl radical or a phenyl radical optionally substituted with an alkyl radical, and
  the symbol R' represents:
either a radical of general formula (IIa) in which the symbols $R_1$ and $R_2$, which may be identical or different, represent alkyl radicals or, together with the nitrogen atom to which they are attached, form a saturated 4- to 5-membered heterocycle and the symbol $R_3$ represents a phenethyl radical or an alkyl radical optionally substituted with a cycloalkyl radical containing 3 to 6 carbon atoms, or a radical of general formula (IIb), and in particular:
  1-methyl-1-[2-(propylcarbamoyl-10-phenothiazinyl)-propyl]pyrrolidinium
  1-phenethyl-1-[2-(2-propylcarbamoyl-10-phenothiazinyl)propyl]pyrrolidinium
  1-methyl-1-{2-[2-(3-methylbutyl)carbamoyl-10-phenothiazinyl]propyl}pyrrolidinium
  1-methyl-1-{2-[2-(2-methylphenyl)-methyl-carbamoyl-10-phenothiazinyl]propyl}pyrrolidinium
  10-[1-(1-pyrrolidinyl N-oxide)-2-propyl]-N-propyl-2-phenothiazinecarboxamide.

EXAMPLES

The examples which follow, given without implied limitation, illustrate the present invention.

EXAMPLE 1

A solution of N-propyl-10-[1-(1-pyrrolidinyl)-2-propyl]-2-phenothiazinecarboxamide, L series (1.1 g), and methyl iodide (0.75 cc) in acetone (40 cc) is stirred for 2 days at a temperature in the region of 20° C. The pale yellow solution thereby obtained is concentrated to dryness under reduced pressure (30 mm Hg; 4 kPa) at 40° C. and the light cream-colored meringue-like residue is suspended with stirring for 30 minutes in diethyl ether (50 cc), drained, washed with diethyl ether (3×10 cc) and dried at 40° C. under reduced pressure (5 mm Hg; 0.7 kPa). 1-Methyl-1-[2-(2-propylcarbamoyl-10-phenothiazinyl)propyl]pyrrolidinium iodide, L series (1.2 g), is thereby obtained in the form of a light beige solid, m.p. 155°-160° C.

$[\alpha]_D^{20} = +9.0 \pm 0.5°$ (0.98%; dimethylformamide).

Proton NMR (250 MHz, DMSO-d$_6$, δ in ppm, J in Hz).

0.92 (T, J=7, 3H, propyl—CH$_3$); 1.56 sextet, J=7, 2H, propyl—CH$_2$—); 1.92 (D, J=6.5, 3H, —CH$_3$); 2 (Mt, 4H, pyrrolidine —CH$_2$—); 3.01 (S, 3H, NCH$_3$); 3.25 (TD, J=7 and 5.5, 2H, —CO—NH—CH$_2$—); 3.30 and 3.60 (2 Mt, 1H and 3H respectively, pyrrolidine→⊕N—CH$_2$); 3.78 (DD, J=14 and 1.5, 1H of→ ⊕N—CH$_2$—); 4.12 (DD, J=14 and 9, 1H of→ ⊕N—CH$_2$—); 4.83 (Mt, J=9, 6.5 and 1.5, 1H, N—CH); 7.05 to 7.4 (Mt, 5H, aromatic); 7.56 (D, J=8, 1H, —H at 3-position); 7.57 (S, 1H, —H at 1-position); 8.53 (T, J=5.5, 1H, —CONH—).

Infrared spectrum (KBr), characteristic bands in cm$^{-1}$: 3300, 2960, 2925, 2870, 1640, 1590, 1555, 1535, 1460, 870, 830, 755.

N-Propyl-10-[1-(1-pyrrolidinyl)propyl]-2-phenothiazinecarboxamide, L series, may be prepared in the following manner:

Fumaric acid (2.7 g) is added to a solution of N-propyl-10-[1-(1-pyrrolidinyl)-2-propyl]-2-phenothiazinecarbothioamide, L series (9.5 g), in ethanol (100 cc). The solution obtained is concentrated to dryness under reduced pressure (300 mm Hg; 4 kPa) at 40° C. The meringue-like yellow residue is taken up with acetic acid (200 cc). Mercuric acetate (7.3 g) is added to the solution obtained and the mixture is stirred for 16 hours at a temperature in the region of 20° C. The black suspension obtained is diluted with distilled water (200 cc) and filtered. The yellow filtrate is concentrated under reduced pressure (30 mm Hg; 4 kPa) at 40° C. The residue is taken up with ethyl acetate (250 cc) and distilled water (50 cc) and then treated with sodium hydroxide (d=1.33) to pH 13. The aqueous phase is separated after settling has taken place and extracted with ethyl acetate (250 cc). The organic phases are combined, washed successively with distilled water (2×100 cc) and with a saturated aqueous sodium chloride solution (100 cc) and dried over magnesium sulphate. After filtration, the yellow filtrate is concentrated under reduced pressure (30 mm Hg; 4 kPa) at 40° C. and a crude yellow oil (9.2 g) is thereby obtained. This residue is purified by chromatography on a column (height: 22 cm; diameter: 4 cm) of silica gel (0.2–0.063 mm), eluting with a mixture of methylene chloride and methanol (95:5 by volume). The first 1500 cc are discarded and the next 1500 cc are concentrated under reduced pressure (30 mm Hg; 4 kPa) at 40° C. to give N-propyl-10-[1-(pyrrolidinyl)-2-propyl]-2-phenothiazinecarboxamide, L series (7.3 g), in the form of a yellow gum.

$[\alpha]_D^{20} = +23.4 \pm 12°$ (0.4%; methanol).

A 3.3N solution (6.2 cc) of hydrochloric acid in isopropyl ether is added dropwise in the course of 5 minutes to a solution of N-propyl-10-[1-(1-pyrrolidinyl)-2-propyl]-2-phenothiazinecarboxamide, L series (7.2 g), in anhydrous ethyl acetate (80 cc). The product deposits on the walls and crystallizes on scratching. The suspension obtained is maintained for one hour at a temperature in the region of 5° C. The solid is drained, washed with anhydrous ethyl acetate (3×5 cc) and dried under reduced pressure (5 mm Hg; 0.7 kPa) at 40° C. to give N-propyl-10-[1-(1-pyrroli-dinyl)-2-propyl]-2-phenothiazinecarboxamide hydrochloride, L series (7.1 g), in the form of a white solid, m.p. 190° C.

$[\alpha]_D^{20} = +19.4 \pm 0.6°$ (0.85%; dimethylformamide).

Proton NMR (250 MHz, DMSO, δ in ppm, J in Hz).
0.9 (T, J=7.5, 3H, —CH$_2$—CH$_3$); 1.57 (Mt, 2H, —CH$_2$CH$_3$); 1.79 (D, J=7, 3H, —CH$_3$); 1.75 to 2 (Mt, 4H, pyrrolidine —CH$_2$CH$_2$—); 2.85, 3.10, 3.60 and 3.75 (4 Comp of 1H each, pyrrolidine —CH$_2$—N—CH$_2$—); 3.24 (Mt, 2H, —CONH—CH$_2$—); 3.77 (AB, 2H, N—CH$_2$—); 4.76 (Mt, 1H, N—CH); 7 to 7.4 (Mt, 5H, aromatic); 7.53 (S, 1H, —H at 1-position); 7.55 (D, J=8, 1H, —H at 3-position); 8.66 (T, J=5.5, 1H, —CONH—); 10.7 (Comp, 1H, —NH+).

Infrared spectrum (KBr), characteristic bands in cm$^{-1}$: 3260, 3060, 2965, 2935, 2880, 2670, 2570, 2470, 1645, 1595, 1535, 1465, 1415, 1380, 1360, 1235, 875, 835, 755.

N-Propyl-10-[1-(1-pyrrolidinyl)-2-propyl]-2-phenothiazinecarbothioamide, L series may be prepared in the following manner:

A mixture of 10-[1-(1-pyrrolidinyl)-2-propyl]-2-phenothiazinecarbothioamide, L series (10.3 g), and propylamine (32 cc) in ethanol (150 cc) is saturated with hydrogen sulphide and then heated for 16 hours at 105° C. in an autoclave. After cooling, the solution is concentrated to dryness under reduced pressure (30 mm Hg; 4 kPa) at 40° C. An orange-colored oil (10.2 g) is obtained, which is purified by chromatography on a column of silica (0.2–0.063 mm) diameter: 4 cm; height: 25 cm), eluting with a 95:5 (by volume) mixture (2 liters) of methylene chloride and methanol and collecting 100-cc fractions. Fractions 13 to 17 are combined and concentrated under reduced pressure (30 mm Hg; 4 kPa) at 40° C. N-Propyl-10-[1-(1-pyrrolidinyl)-2-propyl]-2-phenothiazinecarbothioamide, L series (9.5 g), is obtained in the form of a yellow oil.

$[\alpha]_D^{20} = +30.4 \pm 0.6°$ (1%; methanol).

10-[1-(1-Pyrrolidinyl)-2-propyl]-2-phenothiazine-carbothioamide, L series, may be prepared in the following manner:

A mixture of 10-[1-(1-pyrrolidinyl)-2-propyl]-2-phenothiazinecarbonitrile, L series (11.2 g), and triethylamine (4.7 cc) in anhydrous pyridine (225 cc) is saturated by bubbling in hydrogen sulphide for one hour at 25° C. The mixture is stirred for 20 hours at 25° C. The reaction mixture is outgassed by bubbling in nitrogen and is then diluted with ethyl acetate (500 cc) and washed with distilled water (500 cc). The aqueous phase is extracted again with ethyl acetate (250 cc). The combined organic phases are washed with water (2×200 cc) and saturated aqueous sodium chloride solution (200 cc), dried over magnesium sulphate and concentrated under reduced pressure (30 mm Hg; 4 kPa) at 40° C. An orange-colored oil (14.4 g) is obtained, which is purified by chromatography on a column of silica (0.2–0.63 mm) (diameter: 4 cm; height: 30 cm), eluting with a 95:5 (by volume) mixture (3 liters) of methylene chloride and methanol and collecting 120-cc fractions. Fractions 12 to 27 are combined and concentrated under reduced pressure (30 mm Hg; 4 kPa) at 40° C. 10-[1-(1-Pyrrolidinyl)-2-propyl]-2-phenothiazinecarbothioamide, L series (10.3 g), is obtained in the form of an orange-colored meringue-like product.

$[\alpha]_D^{20} = -43 \pm 0.7°$ (1%; chloroform).

10-[1-(1-Pyrrolidinyl)-2-propyl]-2-phenothiazine-carbonitrile, L series, may be prepared in the following manner:

A mixture of 2-(2-cyano-10-phenothiazinyl)-1-propyl methanesulphonate, L series (25 g), and pyrrolidine (26.6 cc) in toluene (250 cc) is heated for 55 hours to a temperature in the region of 90° C. The reaction mixture is concentrated to dryness under reduced pressure (30 mm Hg; 4 kPa) at 40° C. The residue is taken up with ethyl ether (500 cc) and extracted with 2N aqueous methanesulphonic acid solution (2×100 cc). The aqueous phase is alkalinized with caustic soda at a temperature in the region of 5° C. and extracted with ethyl ether (2×250 cc). The combined organic phases are washed successively with ethyl ether (100 cc). The combined organic phases are washed successively with distilled water (100 cc) and with saturated aqueous sodium chloride solution (100 cc), dried over magnesium sulphate and filtered, and the yellow filtrate is concentrated to dryness under reduced pressure (30 mm Hg; 4 kPa) at 40° C. The orange-colored oil (17.1 g) thereby obtained is chromatographed on a column (height: 45 cm; diameter: 4 cm) of silica gel (0.063–0.2 mm), eluting with a mixture (1 liter) of methylene chloride and methanol (95:5 by volume) and collecting 100-cc fractions. Fractions 3 to 7 are combined and concentrated to dryness under reduced pressure (30 mm Hg; 4 kPa) at 40° C. 10-[1-(1-Pyrrolidinyl)-2-propyl]-2-phenothiazinecarbonitrile, L series (11.2 g), is thereby obtained in the form of a yellow oil.

$[\alpha]_D^{20} = +9.7 \pm 0.3°$ (1.2%; chloroform).

2-(2-Cyano-10-pheothiazinyl)-1-propyl methanesulphonate, L series, may be prepared in the following manner:

Triethylamine (10 cc) is added with stirring to a solution, cooled to a temperature in the region of 5° C., of 10-(1-hydroxy-2-propyl)-2-phenothiazinecarbonitrile, L series (12.6 g), in methylene chloride (126 cc), a solution of methanesulphonyl chloride (5.6 cc) in methylene chloride (56 cc) is then introduced dropwise during 25 minutes and stirring is continued for 1 hour 15 minutes at a temperature in the region of 10°–15° C. The reaction mixture is washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. 2-(2-Cyano-10-phenothiazinyl)-1-propyl methanesulphonate, L series (16.2 g), is thereby obtained in the form of an orange-colored oil $[\alpha]_D^{20} = +29.9 \pm 0.3°$ (2.4%; chloroform), which is used without further purification for the next step of the syntheses.

10-(1-Hydroxy-2-propyl)-2-phenothiazine-carbonitrile, L series, may be prepared in the following manner:

A 1.97M alcoholic solution (84.9 cc) of potassium hydroxide is added to a solution of (+)-[2-(2-cyano-10-phenothiazinyl)propyl (R)-1-phenylethylammonium phthalate] (42 g) in ethanol (420 cc) under reflux, and refluxing is continued with stirring for 15 minutes. The reaction mixture is then poured onto crushed ice (500 g) and extracted with ethyl acetate (500 cc, then 2×250 cc). The organic phases are combined, washed successively with 0.5N aqueous hydrochloric acid solution (200 cc), with 0.1N aqueous hydrochloric acid solution (100 cc), with saturated aqueous sodium hydrogen carbonate solution (2×250 cc) and with saturated aqueous sodium chloride solution (100 cc), dried over magnesium sulphate, filtered and concentrated to dryness under reduced pressure (30 mm Hg; 4 kPa) at 40° C. The residual yellow solid is taken up with isopropyl ether (100 cc), ground, drained, washed with isopropyl ether (10 cc) and dried under reduced pressure (5 mm Hg; 0.7 kPa) at 40° C. 10-(1-Hydroxy-2-propyl)-2-phenothiazinecarbonitrile, L series (17.8 g), is thereby obtained in the form of yellow crystals, m.p. 136° C.

$[\alpha]_D^{20} = -13 \pm 0.4°$ (1.2%; chloroform).

(+)-[2-(2-Cyano-10-phenothiazinyl)propyl (1R)-1-phenylethylammonium phthalate] may be prepared in the following manner:

A suspension of 10-[(2RS)-1-hydroxy-2-propyl]-2-phenothiazinecarbonitrile (56.5 g) and phthalic anhydride (32.6 g) in anhydrous pyridine (100 cc) is brought to reflux for 6 hours with stirring. After cooling, the reaction mixture is diluted with methylene chloride (500 cc), washed with distilled water (4×100 cc), dried over magnesium sulphate, filtered and concentrated to dryness under reduced pressure (30 mm Hg; 4 kPa) at 40° C. The residue is stirred with N aqueous hydrochloric acid solution (500 cc), then separated after settling has taken place and dissolved in ethyl acetate (500 cc).

The solution is washed with N aqueous hydrochloric acid solution (2×100 cc) and then with aqueous sodium chloride solution (100 cc). The organic phase is dried over magnesium sulphate, filtered and concentrated to dryness under reduced pressure (30 mm Hg; 4 kPa) at 50° C. A thick oil (102 g) containing 2-[(2RS)-2-(2-cyano-10-phenothiazinyl)-1-propyl]oxycarbonylbenzene-carboxylic acid is thereby obtained, and is used subsequently without further treatment.

The oil (102 g) obtained above and containing 2-[(2RS)-2-(2-cyano-10-cyano-10-phenothiazinyl)-1-propyl]oxy-carbonylbenzenecarboxylic acid is dissolved in ethyl acetate (500 cc), and a solution of (−)-(1S)-1-phenylethylamine (24.2 g) in ethyl acetate (360 cc) is added with stirring at a temperature in the region of 20° C. After 2 days' stirring at a temperature in the region of 20° C., the solid formed is filtered off and stored.

The filtrate is concentrated to dryness under reduced pressure (30 mm Hg; 4 kPa) at 40° C. The residue is taken up with N aqueous hydrochloric acid solution (500 cc) and extracted with ethyl acetate (2×250 cc). The combined organic phases are concentrated to dryness under reduced pressure (30 mm Hg; 4 kPa) at 40° C. The residue (50 g) is dissolved in ethyl acetate (500 cc) and (+)-(1R)-1-phenylethylamine (14 g) is added. After 16 hours' stirring at a temperature in the region of 20° C., the solid formed is drained and dissolved in ethyl acetate (450 cc) under reflux. After cooling, the solid formed is drained, washed with ethyl acetate (40 cc) and dried under reduced pressure (50 mm Hg; 4 kPa) at 40° C. (+)-[2-(2-Cyano-10-phenothiazinyl)-propyl (1R)-1-phenylethylammonium phthalate] (44.3 g) is thereby obtained in the form of light yellow crystals, m.p. 154°–155° C.

$[\alpha]_D^{20} = +20.8 \pm 0.5°$ (1.1%; chloroform).

EXAMPLE 2

A solution of N-propyl-10-[1-(1-pyrrolidinyl)-2-propyl]-2-phenothiazinecarboxamide, L series (1.98 g), and dimethyl sulphate (0.46 cc) in acetone (60 cc) is stirred for 16 hours at a temperature in the region of 20° C. The light yellow solution obtained is concentrated to dryness under reduced pressure (30 mm Hg; 4 kPa) at 40° C. and the pale yellow meringue-like residue is suspended with stirring for 2 hours in diethyl ether (50 cc), drained, washed with diethyl ether (2×5 cc) and dried at 40° C. under reduced pressure (5 mm Hg; 0.7 kPa). 1-Methyl-1-[2-(2-propylcarbomoyl-10-phenothiazinyl)propyl]pyrrolidinium methylsulphate, L series (2.45 g), is thereby obtained in the form of a hygroscopic, very light cream colored meringue-like solid, m.p. about 150°–160° C.

$[\alpha]_D^{20} = +22.9 \pm 0.6°$ (0.88%; methanol).

Proton NMR (250 MHz, DMSO-d$_6$, δ in ppm, J in Hz).

0.91 (T, J=7, 3H, propyl —CH$_3$); 1.56 (sextet, J=7, 2H, propyl —CH$_2$); 1.92 (D, J=7, 3H, —CH$_3$); 2.02 (Mt, 4H, pyrrolidine —CH$_2$—); 3 (S, 3H, →⊕NCH$_3$); 3.25 (Mt, 2H, —CONH—C$\underline{H}_2$—); 3.38 (S, 3H, methylsulphate —CH$_3$); 3.35 to 3.7 (Mt, 4H, pyrrolidine →⊕N—CH$_2$—); 3.77 (broad D, J=14, 1H of →⊕N—CH$_2$—); 4.11 (DD, J=14 and 9, 1H, the other H, →⊕N—CH$_2$—); 4.83 (Mt, J=9, 7 and small, 1H, N—CH); 7.05 to 7.4 (Mt, 5H, aromatic); 7.55 (D, J=8, 1H, —H at 3-position); 7.57 (S, 1H, —H at 1-position); 8.53 (T, J=5.5, 1H, —CONH—).

Infrared spectrum (KBr), characteristic bands in cm$^{-1}$: 2965, 2940, 2875, 1645, 1595, 1560, 1540, 1460, 1250, 1230, 1060, 1010, 875, 825, 750.

EXAMPLE 3

A solution of N-propyl-10-[1-(1-pyrrolidinyl)-2-propyl]-2-phenothiazinecarboxamide, L series (5.5 g), in acetone (15 cc) is introduced, dropwise and with stirring during 30 minutes, into a solution of methyl bromide (9.5 g) in acetone (90 cc), and stirring is maintained for 16 hours at a temperature in the region of 20° C. The suspension obtained is filtered and the solid is washed with acetone (3×1 cc), drained and dried at 40° C. under reduced pressure (5 mm Hg; 0.7 kPa). This amorphous white solid (4.8 g) is dissolved in acetonitrile (12 cc) under reflux. The crystals formed after cooling are drained, washed with ice-cold acetonitrile (3×3 cc) and dried at 40° C. under reduced pressure (5 mm Hg; 0.7 kPa). 1-Methyl-1-[2-(2-propylcarbamoyl-10-phenothiazinyl)propyl]pyrrolidinium bromide, L series (2.05 g), is thereby obtained in the form of a crystalline white solid, m.p. 258° C.

$[\alpha]_D^{20} = +17.0 \pm 0.5°$ (1%; methanol).

Proton NMR (250 MHz, DMSO-d$_6$, δ in ppm, J in Hz).

0.92 (T, J=7, 3H, propyl —CH$_3$); 1.58 (sextet, 2H, propyl —CH$_2$); 1.93 (D, J=7, 3H, —CH$_3$); 2.02 (Mt, 4H, pyrrolidine —CH$_2$—); 3.07 (S, 3H, →⊕NCH$_3$); 3.25 (Mt, J=7 and 5.5, 2H, CONH—CH$_2$—); 3.37 and 3.65 (2 Mt, 1H and 3H respectively, pyrrolidine →⊕—N—CH$_2$—); 3.9 (DD, J=14 and 1, 1H of →⊕N—CH$_2$—); 4.12 (DD, J=14 and 9, 1H, the other H of →⊕N—CH$_2$—); 4.94 (Mt, J=9, 7 and 1, 1H, N—CH); 7 to 7.4 (Mt, 5H, aromatics); 7.57 (D, J=8, 1H, —H at 3-position); 7.6 (S, 1H, H at 1-position); 8.71 (T, J=5.5, 1H, —CONH—).

Infrared spectrum (KBr), characteristic bands in cm$^{-1}$: 3245, 2960, 2925, 2875, 1645, 1590, 1560, 1535, 1460, 875, 840, 750.

EXAMPLE 4

A solution of methyl chloride in a mixture of acetone (10 cc) and dimethylformamide (1.4 cc) is prepared by bubbling in methyl chloride, washed twice beforehand in washing bottles of triethylamine and a washing bottle of ethyl acetate, for 80 minutes at a temperature of in the region of 20° C. N-Propyl-10-[1-(1-pyrrolidinyl)-2-propyl]-2-phenothiazinecarboxamide, L series (1 g), is added to the solution obtained, and the bubbling-in of methyl chloride is continued with stirring for 18 hours at a temperature in the region of 20° C. Stirring is then continued for 5 days. The crystals formed are collected by filtration, washed with acetone (2×1 cc) and dried at 40° C. under reduced pressure (5 mm Hg; 0.7 kPa). 1-Methyl-1-[2-(2-propyl-carbamoyl-10-phenothiazinyl)propyl]pyrrolidinium chloride, L series (0.21 g) is thereby obtained in the form of a crystalline white solid, m.p. 247° C.

$[\alpha]_D^{20} = +14.0 \pm 0.5°$ (0.93%; methanol).

NMR proton (400 MHz, DMSO-d$_6$, δ in ppm, J in Hz).

0.93 (T, J=7, 3H, propyl —CH$_3$); 1.6 (sextet, J=7, 2H, propyl —CH$_2$—); 1.95 (D, J=7, —CH$^3$); 2.03 (Mt, 4H, pyrrolidine —CH$_2$—); 3.1 (S, 3H, →⊕NCH$_3$); 3.26 (Mt, J=7 and 5.5, 2H, —CO—NH—CH$_2$—); 3.4 and 3.67 (2 Mt, 1H and 3H respectively, pyrrolidine →⊕NCH$_2$); 3.9 (DD, J=14 and 1, 1H of →⊕NCH$_2$—); 4.13 (DD, J=13 and 9, 1H, the other H of →⊕N—CH$_2$—); 5.03 (Mt, J=9, 7 and 1, 1H, N—CH); 7.05 to 7.4 (Mt, 5H, aromatic); 7.58 (D, J=8, 1H, —H at 3-position); 7.67 (S, 1H, H at 1-position); 9.05 (T, J=5.5, 1H, —CONH—).

Infrared spectrum (KBr), characteristic bands in cm$^{-1}$. 3240, 2960, 2930, 2870, 1640, 1590, 1555, 1540, 1460, 875, 830, 750.

EXAMPLE 5

A saturated aqueous sodium chloride solution (35 cc) is added in the course of 10 minutes with stirring at 20° C. to a solution of 1-methyl-1-[2-(2-propylcarbamoyl-10-phenothiazinyl)propyl]pyrrolidinium methylsulphate, L series (6.15 g), in distilled water (10 cc). The oil formed is then allowed to settle, the mixture is cooled to a temperature in the region of 0° C. for 90 minutes and the supernatant is thereafter removed. The yellow oil is taken up in distilled water (3.5 cc) and saturated aqueous sodium chloride solution (17 cc) is added. The emulsion formed is separated after settling has taken place and cooled for 2 hours to a temperature in the region of 0° C., and the supernatant is removed. The yellow oil formed is dissolved in acetonitrile (80 cc) and the solution is dried 3 times over magnesium sulphate, filtered and concentrated to dryness under reduced pressure (30 mm Hg; 4 kPa) under a dry atmosphere at 50° C. The yellow meringue-like residue thereby obtained (4.52 g) is subjected to an azeotropic distillation in solution in 1,2-dichloroethane (80 cc) in order to remove the final traces of water, and the solution is then concentrated to dryness under reduced pressure (5 mm Hg; 0.7 kPA) at 20° C. under a dry atmosphere. The yellowish meringue-like residue thereby obtained (5 g) is stirred for 2 hours in suspension in anhydrous diethyl ether (100 cc), filtered, washed with diethyl ether (2×5 cc), drained and dried under reduced pressure (5 mm Hg; 0.7 kPa) at 37° C. 1-Methyl-1-[2-(2-propylcarbamoyl-10-phenothiazinyl)propyl]pyrrolidinium chloride, L series (4.5 g), is thereby obtained in the form of an amorphous white solid, m.p. about 240° C., the infrared spectrum of which is identical to that of the product of Example 4.

$[\alpha]^{20}_D = +22.6 \pm 0.5°$ (1%; methanol).

EXAMPLE 6

Using the procedure described in Example 1, starting with N-propyl-10-[(2RS)-1-(1-pyrrolidinyl)-2-propyl]-2-phenothiazinecarboxamide (3 g), 1-methyl-1-[(2RS)-2-(2-propylcarbamoyl-10-phenothiazinyl)propyl]-pyrrolidinium iodide (3.53 g) is obtained in the form of a pale yellow solid, m.p. about 140° C., the NMR spectrum of which is identical to that of the product obtained in Example 1.

Infrared spectrum (KBr), characteristic bands in cm$^{-1}$: 3275, 2955, 2925, 2870, 1640, 1590, 1560, 1460, 1530, 870, 825, 750.

N-Propyl-10-[(2RS)-1-(1-pyrrolidinyl)-2-propyl]-2phenothiazinecarboxamide may be prepared in the following manner:

Mercuric acetate (0.38 g) is added with stirring to a solution of N-propyl-10-[(2RS)-1-(1-pyrrolidinyl)-2-propyl]-2-phenothiazinecarbothioamide neutral fumarate (0.6 g) in acetic acid (10 cc), and stirring is continued for 4 hours 30 minutes at a temperature in the region of 20° C. The black reaction mixture is diluted with distilled water (25 cc) and ethyl acetate (50 cc) and then filtered and alkalinized with stirring with 4N aqueous sodium hydroxide solution to pH 13. After settling has taken place, the organic phase is separated and the aqueous phase is extracted with ethyl acetate (20 cc). The combined organic phases are washed successively with saturated aqueous sodium chloride solution (50 cc). After drying over magnesium sulphate, filtration and concentration to dryness under reduced pressure (30 mm Hg; 4 kPa) at 40° C., N-propyl-10-[(2RS)-1-(1-pyrrolidinyl)-2-propyl]-2-phenothiazinecarboxamide (0.43 g) is obtained in the form of a yellow oil.

EXAMPLE 7

A solution of N-propyl-10-[1-(1-pyrrolidinyl)-2-propyl]-2-phenothiazinecarboxamide, L series (1 g), and ethyl iodide (1 cc) in acetonitrile (50 cc) is stirred for 24 hours at a temperature in the region of 60° C. The pale yellow solution thereby obtained is concentrated to dryness under reduced pressure (30 mm Hg; 4 kPa) at 40° C., and the light cream-colored meringue-like residue is suspended with stirring for 30 minutes in diethyl ether (50 cc), drained, washed with diethyl ether (3×10 cc) and dried at 40° C. under reduced pressure (5 mm Hg; 0.7 kPa). 1-Ethyl-1-[2-(2-propylcarbamoyl-10-phenothiazinyl)propyl]pyrrolidinum iodide, L series (1 g), is thereby obtained in the form of a light beige solid, m.p. about 125°–130° C.

$[\alpha]_D^{20} = +28.6 \pm 0.6°$ (1.04%; methanol).

Proton NMR (250 MHz, DMSO-d$_6$+small amount of CD$_3$COOD, $\delta$ in ppm and J in Hz).

0.86 (T, J=7, 3H, propyl —CH$_3$); 1.07 (broad T, J=7, 3H, —CH$_2$CH$_3$); 1.53 (sextet, J=7, 2H, propyl —CH$_2$—); 1.95 (D, J=6.5, —CH$_3$); 1.98 (Mt, 4H, pyrrolidine —CH$_2$—); 3.22 (TD, J=7 and 5.5, —CO—N-H—CH$_2$—); 3.15 to 3.65 (Mt, 7H, pyrrolidine →$_\oplus$N—CH$_2$—, →$_\oplus$N—CH$_2$—CH$_3$ and 1H of →$_\oplus$N—CH$_2$—); 4.05 (DD, J=14 and 9, 1H, 1H of →$_\oplus$N—CH$_2$—); 4.72 (Mt, 1H, N—CH); 7 to 7.35 (Mt, 5H, aromatic); 7.52 (D, J=8, 1H, —H at 3-position); 7.56 (S, 1H, H at 1-position); 8.4 (residual T, J=5.5, —CONH—).

Infrared spectrum (KBr), characteristic bands in cm$^{-1}$: 3270, 2960, 2930, 2870, 1640, 1590, 1555, 1530, 1460, 870, 825, 755.

EXAMPLE 8

A suspension of N-propyl-10-[1-(1-pyrrolidinyl)-propyl]-2-phenothiazinecarboxamide, L series (0.6 g), cyclopropylmethyl bromide (0.74 cc), sodium carbonate (1 g) and sodium iodide (0.5 g) in a mixture of acetone (25 cc) and dimethylformamide (0.5 cc) is brought to reflux with stirring for 40 hours, cooled and filtered, and the filtrate is concentrated to dryness under reduced pressure (30 mm Hg; 4 kPa) at 55°–60° C. The orange-colored oily residue (1.98 g) is taken up with stirring with isopropyl ether (35 cc) for 16 hours at a temperature in the region of 20° C. The suspension obtained is filtered and the solid is drained, washed with isopropyl ether (2×10 cc) and dried under reduced pressure (5 mm Hg; 0.7 kPa) at 37° C. This yellow solid (1.25 g) is taken in dichloromethane (12 cc) with stirring for 2 hours and the suspension obtained is filtered. The filtrate is concentrated to dryness under reduced pressure (30 mm Hg; 4 kPa) at 40° C. and the orange-colored oily residue (0.69 g) is solidified by stirring for one hour in diethyl ether (30 cc). The solid formed is separated by filtration, washed with diethyl ether (2×5 cc), drained and dried under reduced pressure (5 mm Hg; 0.7 kPa) at 37° C. 1-Cyclopropylmethyl-1-[2-propyl]-pyrrolidinium iodide, L series (0.59 g), is thereby obtained in the form of an orange-yellow solid, m.p. about 125°–130° C.

$[\alpha]_D^{20} = +21.3 \pm 0.7°$ (0.79%; methanol).

Proton NMR (250 MHz, DMSO-d$_6$, $\alpha$ in ppm and J in Hz).

0.34 and 0.57 (2Mt, 2H, each one cycloylpropylmethyl —CH$_2$—); 0.88 (Mt, 1H, cyclopropylmethyl —CH—); 0.92 (T, J=7, 3H, propyl —CH$_3$); (sextet, J=7, 2H, propyl —CH$_2$—); 1.95 (D, J=7, 3H, —CH$_3$); 1.95 (Mt, 4H, pyrrolidine —CH$_2$—); 3.1 to 3.5 (Mt, 2H, cyclopropyl-methyl →$_\oplus$N—CH$_2$—); 3.25 (Mt, 2H, —CONH—CH$_2$—); 3.35 and 3.57 (2 Mt, the 1st partially masked, 1H and 3H respectively, pyrrolidine →$_\oplus$N—CH$_2$—); 3.74 (broad D, J=14, 1H, 1H, of →$_\oplus$N—CH$_2$—); 4.15 (DD, J=14 and 19, 1H, the other H of →$_\oplus$N—CH$_2$—); 4.77 (Mt, J=9, 7 and broad, 1H, N—CH); 7.05 to 7.4 (Mt, 5H, aromatic); 7.55 (DD, J=8 and 1, 1H, —H at 3-position); 7.58 (D, J=1, 1H, H at 1-position); 8.52 (T, J=5.5, 1H, —CONH—).

Infrared spectrum (KBr), characteristic bands in cm$^{-1}$: 3270, 2960, 2930, 2870, 1640, 1590, 1555, 1530, 1460, 870, 830, 755.

EXAMPLE 9

Potassium carbonate (2.1 g) and sodium iodide (0.1 g) are added to a solution of N-propyl-10-[1-(1-pyrrolidinyl)-2-propyl]-2-phenothiazinecarboxamide, L series (2.16 g), and 2-bromoacetophenone (2.5 g) in acetonitrile (25 cc), and the mixture is brought to reflux with stirring for 4 hours. After cooling, the reaction mixture is filtered and concentrated to dryness under reduced pressure (30 mm Hg; 4 kPa) at 40° C. The residue is purified by chromatography on a column (height: 25 cm; diameter: 3.6 cm) of silica gel (0.04–0.063 mm) under a slight excess pressure of nitrogen (40 kPa), eluting successively with a mixture (3 liters) of methylene chloride and methanol (95:5 by volume) and then with a mixture (2 liters) of methylene chloride and methanol (90:10 by volume) and collecting 75-cc fractions. Fractions 39 to 66 are combined and concentrated to dryness under reduced pressure (30 mm Hg; 4 kPa) at 50° C. The yellow meringue-like residue (0.5 g) is taken up with stirring with isopropyl ether (40 cc) for 1 hour at a temperature in the region of 20° C., drained, washed with isopropyl ether (2×5 cc) and dried under reduced pressure (5 mm Hg; 0.7 kPa) at 40° C. 1-Benzoylmethyl-1-[2-(2-propylcarbamoyl-10-phenothiazinyl)propyl]pyrrolidinium bromide, L series (0.33 g), is thereby obtained in the form of a yellow powder, m.p. about 190° C.

$[\alpha]_D^{20} = +7.3 \pm 0.4°$ (1.1%; methanol).

Proton NMR (250 MHz, DMSO-d$_6$, α in ppm, J in Hz).

0.92 (T, J=7, 3H, propyl —CH$_3$); 1.56 (sextet, J=7, 2H, propyl —CH$_2$—); 1.9 (D, J=7, 3H, —CH$_3$); 2.08 (Mt, 4H, pyrrolidine —CH$_2$—); 3.26 (Mt, 2H, —CONH—CH$_2$—); 3.6 to 4 (Mt, 4H, pyrrolidine →$_\oplus$N—CH$_2$—); 3.8 (broad D, J=14 1H, 1H of →$_\oplus$N—CH$_2$—); 4.7 to 4.95 (Mt, 2H, the other H of N—CH$_2$— and N—CH); 5.3 (AB, J=18, 2H, →$_\oplus$N—CH$_2$—CO—); 6.85 to 7.8 (Mt, 12H, aromatic); 8.55 (T, J=5.5, 1H, —CONH—).

Infrared spectrum (KBr), characteristic bands in cm$^{-1}$: 3280, 2960, 2930, 2875, 1690, 1640, 1590, 1555, 1530, 1460, 870, 835, 755, 685.

EXAMPLE 10

A suspension of N-propyl-10-[1-(1-pyrrolidinyl)-2-propyl]-2-phenothiazinecarboxamide, L series (1 g), phenethyl bromide (3.42 cc) and sodium carbonate (2.6 g) in acetonitrile (20 cc) is stirred for 5 days at a temperature in the region of 60° C. The pale yellow suspension thereby obtained is filtered and concentrated to dryness under reduced pressure (30 mm Hg; 4 kPa) at 40° C., and the light cream-colored meringue-like residue is suspended with stirring for 30 minutes in diethyl ether (50 cc), drained, washed with diethyl ether (3×10 cc) and dried at 40° C. under reduced pressure (5 mm Hg; 0.7 kPa). 1-Phenethyl-1-[2-(2-propylcarbamoyl-10-phenothiazinyl)propyl]-pyrrolidinium iodide, L series (1.2 g), is thereby obtained in the form of a beige solid, m.p. about 145°–150° C.

$[\alpha]_D^{20} = +4.0 \pm 0.5°$ (0.8%; methanol).

Proton NMR (250 MHz, DMSO-d$_6$, α in ppm, J in Hz).

0.92 (T, J=7, 3H, propyl —CH$_3$); 1.58 (sextet, J=7, 2H, propyl —CH$_2$—); 1.98 (D, J=6.5, —CH$_3$); 1.8 to 2.15 (Mt, 4H, pyrrolidine —CH$_2$—); 3 (Mt, 2H, phenethyl —CH$_2$—); 3.21 (TD, J=7 and 5.5, 2H, —CO—N—H—CH$_2$—); 3.30 to 3.80 (Mt, 6H, pyrrolidine →$_\oplus$N—CH$_2$— and phenethyl →$_\oplus$N—CH$_2$—); 3.88 (broad D, J=14, 1H, 1H of →$_\oplus$N—CH$_2$—); 4.11 (DD, J=14 and 7.5, 1H, 1H of N—CH); 7.05 to 7.4 (Mt, 10H, aromatic); 7.57 (DD, J=8 and 1, 1H, —H at 3-position); 7.62 (D, J=1, 1H, —H at 1-position); 8.6 (T, J=5.5, 1H, —CONH—).

Infrared spectrum (KBr), characteristic bands in cm$^{-1}$: 3250, 2960, 2930, 2875, 1640, 1590, 1560, 1535, 1460, 875, 830, 755, 700.

EXAMPLE 11

A solution of N-(3-methylbutyl)-10-[(1RS)-1-(1-pyrrolidinyl)-2-propyl)-2-propyl]-2-phenothiazinecarboxamide (0.75 g) and methyl iodide (0.25 g) in dimethylformamide (5 cc) is stirred for 16 hours at a temperature in the region of 20° C. The yellow solution thereby obtained is treated with isopropyl either (250 cc) with stirring. The gum which settles out is separated and solidified in isopropyl ether (100 cc), and the solid formed is drained, washed with isopropyl ether (2×5 cc) and dried under reduced pressure (5 mm Hg; 0.7 kPa) at 40° C. 1-Methyl-1-{(2RS)-2-[2-(3-methylbutyl)-carbamoyl-10-phenothiazinyl]propyl}-pyrrolidinium iodide (0.76 g) is thereby obtained in the form of a cream-colored powder, m.p. about 160°–162° C.

Proton NMR (250 MHz, DMSO-d$_6$, α in ppm, J in Hz).

0.93 (D, J=7, 6H, 3-methylbutyl —CH$_3$); 1.45 (Q, J=7, 2H, 3-methylbutyl —CH$_2$—); 1.62 (Mt, 1H, 3-methyl-butyl —CH—); 1.91 (D, J=6.5, 3H, —CH$_3$); 2 (Mt, 4H, pyrrolidine —CH$_2$—); 3.01 (S, 3H, →$_\oplus$NCH$_3$); 3.30 (Mt, 2H, 3 methylbutyl —CONHCH$_2$—); 3.30 and 3.58 (2 Mt, 1H and 3H respectively, pyrrolidine →$_\oplus$NCH$_2$—); 3.79 (broad D, J=14, 1H, 1H of →$_\oplus$NCH$_2$); 4.10 (DD, J=14 and 9, 1H, 1H of →$_\oplus$NCH$_2$); 4.83 (Mt, J=9, 6.5 and 1, 1H, N—CH); 7.05 to 7.4 (Mt, 5H, aromatic); 7.55 (D, J=8, 1H, —H at 3-position); 7.5 (S, 1H, H at 1-position); 8.48 (T, J=5.5, 1H, —CONH—).

Infrared spectrum (KBr), characteristic bands in cm$^{-1}$: 3270, 2950, 2870, 1640, 1590, 1555, 1530, 1460, 1380, 1365, 870, 830, 755.

Mercuric acetate (0.668 g) is added with stirring to a suspension of N-(3-methylbutyl-10-[(2RS)-1-(1-pyrrolidinyl)-2-propyl]-2-phenothiazinecarbothioamide hydrochloride (1 g) in acetic acid (20 cc), and the mixture is allowed to react for 5 hours 30 minutes at a temperature in the region of 20° C. The reaction mixture is diluted with ethyl acetate (150 cc)N and distilled water (50 cc) and then treated with caustic soda (d=1.33) to pH 13. The organic phase is separated and the aqueous phase is extracted again with ethyl acetate (2×50 cc). The combined organic phases are washed with a saturated aqueous sodium hydrogen carbonate solution (100 cc) and then with saturated aqueous sodium chloride solution (100 cc), dried over magnesium sulphate, filtered and concentrated to dryness under reduced pressure (30 mm Hg; 4 kPa) at 40° C. The residual yellow oil (0.53 g) is purified by chromatography on a column (height: 30 cm; diameter: 2.5 cm) of silica gel (0.04–0.063 mm) under a slight excess pressure of nitrogen (40 kPa), eluting successively with a mixture (100 cc) of methylene chloride and methanol (97.5:2.5 by volume) and then with a mixture (200 cc) of methylene chloride and methanol (95:5 by volume) and collecting 15-cc fractions. Fractions 12 to 34 are combined and concentrated to dryness under reduced pressure (30 mm Hg; 4 kPa) at 40° C. N-(3-Methylbutyl)-10-[(2RS)-1-(1-pyrrolidinyl)-2-propyl]-2-phenothiazinecarboxamide (0.6 g) is thereby obtained in the form of a yellow oil.

N-(3-Methylbutyl)-[(2RS)-1-(1-pyrrolidinyl)-2-propyl]-2-phenothiazinecarbothioamide hydrochloride may be prepared in the following manner:

A solution of 10-[(2RS)-1-(1-pyrrolidinyl)-2-propyl]-2-phenothiazinecarbothioamide (1.89 g) and 3-methylbutylamine (8.9 cc) in absolute ethanol (28 cc) is saturated with hydrogen sulphide and this mixture is heated for 16 hours to a temperature in the region of 110° C. After cooling, the reaction mixture is concentration to dryness under reduced pressure (300 mm Hg; 4 kPa) at 40° C., and the oily yellow residue (2.8 g) is purified by chromatography on a column (height: 30 cm; diameter: 2 cm) of silica gel (0.04–0.063 mm) under a slight excess pressure of nitrogen (40 kPa), eluting successively with methylene chloride (100 cc) and then a mixture (300 cc) of methylene chloride and methanol (95:5 by volume) and collecting 30-cc fractions. Fractions 4 to 8 are combined and concentrated to dryness under reduced pressure (30 mm Hg; 4 kPa) at 40° C. The oily yellow residue (2.1 g) is dissolved in ethyl acetate (15 cc) and a 3N solution (2 cc) of hydrochloric acid in ethyl ether is added. The mixture is kept stirred for 1 hour at a temperature in the region of 5° C. The precipitate formed is drained, washed with ethyl acetate (2 cc) and dried under reduced pressure (5 mm Hg; 0.7 kPa) at 35° C. N-(3-Methylbutyl)-10-[(2RS)-1-(1-pyrrolidinyl)-2-propyl]-2-phenothiazinecarbothioamide hydrochloride (2.1 g) is thereby obtained in the form of yellow crystals, m.p. 190° C.

EXAMPLE 12

A solution of N-(3-methylbutyl)-10-[1-(1-pyrrolidinyl)-2-propyl]-2-phenothiazinecarboxamide, L series (1.5 g), and methyl iodide (0.94 cc) in acetone (50 cc) is stirred for 4 days at a temperature in the region of 20° C. The light yellow solution obtained is concentrated to dryness under reduced pressure (30 mm Hg; 4 kPa) at 40° C., and the light cream-colored meringue-like residue is suspended with stirring for 10 minutes in diethyl ether (100 cc), drained, washed with diethyl ether (2×10 cc) and dried at 40° C. under reduced pressure (5 mm Hg, 0.7 kPa). 1-Methyl-1-{2-[2-(3-methylbutyl)carbamoyl-10-phenothiazinyl]propyl}-pyrrolidinium iodide, L series (1.55 g) is thereby obtained in the form of a light beige powder, m.p. about 125°–130° C., the NMR spectrum of which is identical to that of the product of Example 11.

$[\alpha]_D^{20} = +8.5 \pm 0.5°$ (0.94%;dimethylformamide).

Infrared spectrum (KBr), characteristic bands in cm$^{-1}$: 3280, 2960, 2870, 1645, 1590, 1560, 1530, 1460, 1385, 1365, 875, 830, 755.

N-(3-Methylbutyl)-10-[1-(1-pyrrolidinyl)-2-propyl]-2-phenothiazinecarboxamide, L series, may be prepared in the following manner:

Fumaric acid (1.5 g) is added to a solution of N-(3-methylbutyl)-10-[1-(1-pyrrolidinyl)-2-propyl]-2-phenothiazinecarboxamide, L series (4.57 g), in absolute ethanol (100 cc) and the mixture is concentrated to dryness under reduced pressure (30 mm Hg; 4 kPa) at 40° C. The yellow meringue-like residue is taken up with acetic acid (100 cc), mercuric acetate (4.3 g) is added with stirring, and stirring is continued for 16 hours at a temperature in the region of 20° C. The black suspension obtained is concentrated to one quarter of its volume under reduced pressure (30 mm Hg; 4 kPa) at 50° C., taken up with distilled water (200 cc) and filtered. The filtrate is alkalinized with caustic soda (d=1.33) to pH 13 and extracted with ethyl acetate (2×200 cc). The combined organic phases are washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. N-(3-Methylbutyl)-10-[1-(1-pyrrolidinyl)-2-propyl]-2-phenothiazinecarboxamide, L series (4.88 g), is thereby obtained in the form of a slightly yellow oil. A portion (3.3 g) of this oil is dissolved in ethyl acetate (25 cc), stirred and treated with a 3.3N solution (2.4 cc) of hydrochloric acid in isopropyl ether, then stirred again for 1 hour at a temperature in the region of 5° C. The solid formed is drained, washed with ethyl ether (3×100 cc) and dried under reduced pressure (5 mm Hg; 0.7 kPa) at 40° C. N-(3-Methylbutyl)-10-[1-(1-pyrrolidinyl)-2-propyl]-2-phenothiazinecarboxamide hydrochloride, L series (2.55 g), is thereby obtained in the form of a white solid, m.p. 210° C.

$[\alpha]_D^{20} = +14 \pm 0.9°$ (0.5%;dimethylformamide).

Infrared spectrum (KBr), characteristic bands in cm$^{-1}$: 3295, 3060, 2950, 2870, 2680, 2620, 2485, 1660, 1650, 1595, 1535, 1460, 1410, 1380, 1360, 1305, 1230, 855, 825, 750.

N-(3-Methylbutyl)-10-[1-(1-pyrrolidinyl)-2-propyl]-2-phenothiazinecarboxamide, L series, may be prepared in the following manner:

A solution of 10-[1-(1-pyrrolidinyl)-2-propyl]-2-phenothiazinecarboxamide, L series (6 g), and 3-methylbutylamine (18.9 cc) in absolute ethanol (90 cc) is saturated with hydrogen sulphide and brought for 16 hours to a temperature in the region of 105° C. After cooling, the reaction mixture is concentrated to dryness under reduced pressure (30 mm Hg; 4 kPa) at 40° C. The oily brown residue is purified by chromatography on a column (height: 40 cm, diameter: 4 cm) of silica gel (0.02–0.063 mm), eluting with methylene chloride (1 liter) and then with a mixture (1.5 liters) of methylene chloride and methanol (95:5 by volume) and collecting 80-cc fractions. Fractions 23 to 36 are combined and concentrated to dryness under reduced pressure (30 mm Hg; 4 kPa) at 40° C. N-(3-Methylbutyl)-10-[1-(1-pyrrolidinyl) -2-propyl]-2-phenothiazinecarboxamide, L series (6.76 g), is thereby obtained in the form of an orange-colored oil.

EXAMPLE 13

A solution of N-(3-methylbutyl)-10-[(1RS)-1-piperidino-2-propyl]-2-phenothiazinecarboxamide (1.09 g) and methyl iodide (0.36 g) in dimethyl-formamide (10 cc) is stirred for 16 hours at a temperature in the region of 20° C. The yellow solution thereby obtained is treated with isopropyl ether (80 cc) with stirring. The gum which settles out is separated and solidified in isopropyl ether (2×80 cc) and the solid formed is taken up in acetone (15 cc). The solution obtained is introduced dropwise and with stirring into isopropyl ether (150 cc) and the solid formed is drained, washed with isopropyl ether (3×15 cc) and dried at 50° C. under reduced pressure (5 mm Hg; 0.7 kPa). 1-Methyl-1-{(2RS)-2-[2-(3-methylbutyl) carbamoyl-10-phenothiazinyl]propyl}-piperidinium iodide (1.19 g) is thereby obtained in the form of a cream-colored powder, m.p. about 177°-179° C.

Proton NMR (400 MHz, DMSO-d$_6$, α in ppm, J in Hz).

0.89 (D, J=7, 6H, 3-methylbutyl —CH$_3$); 1.41 (Q, J=7, 2H, 3-methylbutyl—CH$_2$—); 1.6 (Mt, 1H, 3-methylbutyl CH—); 1.30 to 1.50 and 1.55 to 1.87 (2 Comp, 3H each, piperidine —CH$_2$—); 1.90 (D, J=6.5, 3H, —CH$_3$); 3.01 (S, 3H, →$_{61}$ NCH$_3$); 3.2 to 3.5 (Mt, 6H, piperidine →$_\oplus$NCH$_2$ and —CO—NH—CH$_2$); 3.66 (DD, J=14 and 1.5, 1H, 1H of →$_\oplus$NCH$_2$—); 4.07 (DD, J=14 and 9, 1H, 1H of →$_\oplus$NCH$_2$—); 4.81 (Mt, J=9, 6.5 and 1.5, 1H, N—CH); 7 to 7.35 (Mt, 5H, aromatic); 7.52 (D, J=8, 1H, —H at 3-position); 7.55 (S, 1H, H at 1-position); 8.47 (T, J=5.5, 1H, —CONH—).

Infrared spectrum (KBr), characteristic bands in cm$^{-1}$ 3280, 2950, 2860, 1640, 1590, 1555, 1530, 1460, 1380, 1360, 865, 830, 755.

N-(3-Methylbutyl)-10-[(2RS)-1-piperidino-2-propyl]-2-phenothiazinecarboxamide may be prepared in the following manner:

A solution of mercuric acetate (1.63 g) in acetic acid (20 cc) is added dropwise during a period of 10 minutes to a solution of N-(3-methylbutyl)-10-[(2RS)-1-piperidino-2-propyl]-2-phenothiazinecarbothioamide (2.32 g) in glacial acetic acid (20 cc). The reaction mixture is stirred for 60 minutes at 25° C. and then filtered on sintered glass covered with Celite. The Celite is washed with ethyl acetate (2×10 cc) and the combined filtrates are concentrated to dryness under reduced pressure (30 mm Hg; 4 kPa) to give a residue which is diluted in ethyl acetate (100 cc). The organic phase is washed with normal sodium hydroxide (2×50 cc) and distilled water (2×50 cc) and then with brine (1×50 cc), dried over magnesium sulphate, filtered and concentrated to dryness under reduced pressure (30 mm Hg; 4 kPa) at 50° C. to give a residue which is purified by chromatography on a column (height: 36 cm; diameter: 2 cm) of silica gel (0.06-0.2 mm), eluting with 80:20 and 50:50 (by volume) mixtures (500 cc and 600 cc, respectively) of cyclohexane and ethyl acetate and collecting 50-cc fractions. Fractions 8 to 20 are combined and concentrated to dryness under reduced pressure (30 mm Hg; 4 kPa) at 50° C. to given N-(3-methylbutyl)-10-[(2RS)-1-piperidino-2-propyl]-2-phenothiazinecarboxamide (0.95 g) in the form of a yellow oil.

N-(3-Methylbutyl)-10-[(2RS)-1-piperidino-2-propyl]-2-phenothiazinecarbothioamide may be obtained in the following manner:

3-Methylbutylamine (4.65 cc) is added to a solution of 10-[(2RS)-1-piperidinio-2-propyl]-2-phenothiazinecarbothioamide (3.07 g) in absolute ethanol (65 cc). The mixture is brought to 150° C. for 16 hours. The reaction pressure (30 mm Hg; 4 kPa) at 50° C. The residue is diluted with ethyl acetate (150 cc), the solution obtained is washed with distilled water (3×50 cc), dried over magnesium sulphate and then concentrated to dryness under reduced pressure (30 mm Hg; 4 kPa) and the residue is purified by chromatography on a column (height: 23.2 cm; diameter: 3.6 cm) of silica gel (0.04-0.06 mm) with a slight excess pressure of nitrogen (40 kPa), eluting with 80:20 and 50:50 (by volume) mixtures (1 liter and 2 liters, respectively) of cyclohexane and ethyl acetate and collecting 60-cc fractions. Fractions 5 to 13 are combined and concentrated to dryness at 50° C. under reduced (30 mm Hg; 4 kPa) to give N-(3-methylbutyl)-10-[(2RS)-1-piperidineo-2-propyl]-2-phenothiazinecarbothioamide (2.49 g).

10-[(2RS)-1-Piperidino-2-propyl]-2-phenothiazinecarbothioamide may be obtained in the following manner:

A mixture of 10-[(2RS)-1-piperidino-2-propyl]-2-phenothiazinecarbonitrile (8.74 g) and triethylamine (3.5 cc) in anhydrous pyridine (100 cc) is saturated by bubbling hydrogen sulphide for 3 hours at 25° C. The clear solution obtained is kept stirred for 12 hours at 25° C. and the mixture is then outgassed by bubbling in nitrogen for 2 hours. The reaction mixture is diluted with ethyl acetate (500 cc) and washed with distilled water (10×200 cc). The organic phase is dried over magnesium sulphate and filtered and the filtrate is concentrated to dryness under reduced pressure (30 mm Hg; 4 kPa). The residue is purified by chromatography on a column (height: 54 cm; diameter: 3.6 cm) of silica gel (0.06-0.2 mm), eluting with a 50:50 (by volume) mixture (1.25 liters) of cyclohexane and ethyl acetate and then with pure ethyl acetate (1.25 liters) and collecting 125-cc fractions. Fractions 4 to 18 are combined and concentrated to dryness under reduced pressure (30 mm Hg; 4 kPa) at 50° C. to give 10-[(2RS)-1-piperidino-2-propyl]-2-phenothiazinecarbothamide (9.36 g).

Proton NMR (250 MHz, DMSO, α in ppm, J in Hz).
1.38 (Mt, 2H, —CH$_2$—CH$_2$—CH$_2$—); 4.23 (Mt, J=7, 6.5 and 6, 1H, N—CH); 6.9 to 7.25 (Mt, 5H, aromatic); 7.43 (broad D, J=8, 1H, —H at 3-position); 7.79 (broad S, 1H, —H at 1-position); 9.5 and 9.9 (2S, 1H each, —CSNH$_2$).

10-[(2RS)-1-Piperidino-2-propyl]-2-phenothiazinecarbonitrile may be obtained in the following manner:

Piperidine (19.8 cc) is added to a suspension of 2-(2-cyano-10-phenothiazinyl)-1-propyl methane-sulphonate (36.05 g) in xylene (360 cc). The mixture is brought to reflux for 19 hours. After cooling, the mixture is washed with distilled water (6×150 cc). The organic phase is dried over magnesium sulphate, filtered and concentrated to dryness at 50° C. under reduced pressure (30 mm Hg; 4 kPa). The residue is purified by chromatography on a column (height: 96 cm; diameter: 4.8 cm) of silica gel (0.06-0.2 mm), eluting with 90:10, 85:15, 80:20 and 75:25 (by volume) mixtures (4 liters, 4 liters and 4 liters, respectively) of cyclohexane and ethyl acetate and collecting 500-cc fractions. The first 9 liters are discarded and fractions 8 to 13 are combined and concentrated to dryness at 50° C. under reduced pressure (30 mm Hg; 4 kPa) to give 10-[(2RS)-1-piperidino-2-propyl]-2-phenothiazinecarbonitrile (13.6 g).

Proton NMR (250 MHz, DMSO, δ in ppm, J in Hz).
1.4 (Mt, 2H, —CH$_2$—CH$_2$—CH$_2$—); 4.19 (Mt, J=7, 6.5 and 6, 1H, N—CH); to 7.35 (Mt, 5H, aromatic); 7.39 (DD, J=8 and 1, 1H, —H at 3-position); 7.79 (D, J=1, 1H, —H at 1-position).

(2RS)-2-(2-Cyano-10-phenothiazinyl)-1-propyl methanesulphonate may be obtained in the following manner:

Triethylamine (100 cc) and then, in the course of 30 minutes, methanesulphonyl chloride (55.9 cc) are introduced with stirring into a solution, cooled to a temperature in the region of 5° C., of 10-[(2RS)-1-hydroxy-2-propyl]-2-phenothiazinecarbonitrile (120.5 g) in methylene chloride (1280 cc), and stirring is continued for 15 minutes while the temperature is maintained at about 10°–15° C. The reaction mixture is diluted with distilled water (500 cc) at 5° C. and the organic phase is separated, washed with saturated aqueous sodium chloride solution (500 cc), dried over sodium sulphate, filtered and concentrated to dryness under reduced pressure (30 mm Hg; 4 kPa) at 40° C. The residual oil (164 g) is purified by chromatography on a column (height: 54 cm; diameter: 8.5 cm) of silica gel (0.2–0.63 mm), eluting with methylene chloride (4.4 liters) and then with a mixture (7 liters) of methylene chloride and methanol (99:1 by volume) and collecting 1-liter fractions. Fractions 3 to 11 are combined and concentrated to dryness under reduced pressure (30 mm Hg; 4 kPa) at 40° C. A yellow oil (153.5 g) is thereby obtained, which is taken up with isopropyl ether (400 cc) under reflex. On cooling, a product crystallizes, and stirring is continued for 1 hour at a temperature in the region of 5° C. The solid formed is drained, washed with ice-cold isopropyl ether (2×50 cc) and dried at 30° C. under reduced pressure (30 mm Hg; 0.4 kPa). (2RS)-2-(2-Cyano-10-phenothiazinyl)-1-propyl methanesulphonate (131.6 g) is thereby obtained in the form of light yellow crystals, m.p. 124° C.

10-[(2RS)-1-Hydroxy-2-propyl]-2-phenothiazine-carbonitrile may be prepared in the following manner:

1,2-Ethanedithiol (113 cc) is introduced with stirring in the course of 15 minutes and at a temperature within the region of 20° C. into a suspension of sodium borohydride (52 g) in tetrahydrofuran (1.4 liters), and a solution of ethyl (2RS)-2-(2-cyano-10-phenothiazinyl) propionate (296 g) in tetrahydrofuran (1.4 liters) is then introduced in the course of 15 minutes under the same conditions. When the addition is complete, the reaction mixture is heated for 20 hours to a temperature in the region of 60° C. After cooling to a temperature in the region 5° C., 4N aqueous sodium hydroxide solution (1 liter) is introduced during 1 hour; a brisk gaseous evolution is observed. The reaction mixture is then poured into a mixture of 4N aqueous sodium hydroxide solution (1 liter) and methylene chloride (3 liters) with stirring. The organic phase is isolated and the aqueous phase is extracted again with methylene chloride (1 liter). The combined organic phases are washed with saturated aqueous sodium chloride solution (2×1 liter), dried over magnesium sulphate, filtered and concentrated to dryness under reduced pressure (30 mm Hg; 4 kPa) at 30° C. The orange-colored viscous oil (290 g) is purified on a column (height: 50 cm; diameter: 8.5 cm) of silica gel (0.2–0.063 mm), eluting successively with methylene chloride (3 liters), then with a mixture (4 liters) of methylene chloride and methanol (97.5:2.5 by volume) and with a mixture (10 liters) of methylene chloride and methanol (95:5 by volume) and collecting 1-liter fractions. Fractions 3 to 15 are combined and concentrated to dryness under reduced pressure (30 mm Hg; 4 kPa) at 30° C. 10-[(2RS)-1-Hydroxy-2-propyl]-2-phenothiazinecarbonitrile (169.7 g) is thereby obtained in the form of a yellow solid, m.p. 123° C.

Ethyl (2RS)-2-(2-cyano-10-phenothiazinyl)-propionate may be obtained in the following manner:

A solution of 2-phenothiazinecarbonitrile (224.5 g) in dimethylformamide (1 liter) is introduced with stirring and in the course of 2 hours 30 minutes into a suspension of sodium hydride (24 g) in dimethylformamide (1 liter) at a temperature in the region of 25° C., an the mixture is left stirring for a further 1 hour 15 minutes until gaseous evolution has ceased. The fine suspension obtained is introduced with stirring in the course of 4 hours 30 minutes and at a temperature in the region of 25° C. into a solution of ethyl (2RS)-2-chloropropionate (255 cc) in dimethylformamide (1 liter) and stirring is continued for 16 hours. Ethanol (100 cc) is then poured into the reaction mixture and the whole is thereafter poured onto a mixture of ice (2 kg) in distilled water (4 liters); a gum precipitates and then crystallizes. The solid formed is drained, washed successively with distilled water (6×500 cc) and petroleum ether (2×500 cc) and dried in the air. Ethyl (2RS)-2-(2-cyano-10-phenothiazinyl)-propionate (296.5 g) is thereby obtained in the form of khaki crystals, m.p. 117°–118° C., which are used without further treatment in the next step.

EXAMPLE 14

Using the procedure described in Example 7, starting with 10-(1-diethylamino-2-propyl)-N-(3-methylbutyl)-2-phenothiazinecarboxamide, L series (0.22 g), and methyl iodide (0.25 cc), 1-methyl-1-{2-[2-(3-methylbutyl) carbamoly -10-phenothiazinyl]}-diethylaminonium iodide (0.23 g) is obtained in the form of a pale yellow solid, m.p. about 120°–130° C.

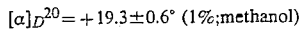

$[\alpha]_D^{20} = +19.3 \pm 0.6°$ (1%;methanol)

Proton NMR (250 MHz, DMSO-d₆, δ in ppm, J in Hz).

0.93 (D, J=7, 6H, 3-methylbutyl —CH₃); 1.45 (Q, J=7, 2H, 3-methylbutyl —CH₂—); 1.62 (Mt, 1H, 3-methylbutyl —CH—); 1.95 (D, J=7, 3H, —CH₃); 2.97 (S, 3H →⊕NCH₃); 3.32 (Mt, partially masked, 4H ethyl →⊕N—CH₂—); 3.64 (broad D, J=14, 1H, 1H of →⊕N—CH₂—); 3.38 (DD, J=14 and 9, 1H and 9, 1H, the other H of →⊕N—CH₂—); 4.78 (Mt, J=9, 7 and broad, 1H, N—CH); 7.05 to 7.45 (Mt, 5H aromatic); 7.55 (D, J=8, 1H, —H at 3-position); 7.58 (broad, S, 1H, H at 1-position); 8.5 (T, J=5.5, 1H, —CONH—).

Infrared spectrum (KBr), characteristic bands in cm⁻¹: 3270, 2955, 2865, 1645, 1590, 1560, 1530, 1460, 870, 830, 755.

10-(1-Diethylamino-2-propyl)-N-(3-methylbutyl)-2-phenothiazinecarboxamide, L series, may be prepared in the following manner:

A solution of 10-(1-diethylamino-2-propyl)-N-(3-methyl-1-butyl)-2-phenothiazinecarbothiamide, L series (2 g), and fumaric acid (0.52 g) in ethanol (20 cc) is concentrated to dryness under reduced pressure (30 mm Hg; 4 kPa) at 40° C. The residue is taken up with stirring with acetic acid (35 cc), mercuric acetate (1.5 g) is then added and stirring is continued at a temperature in the region of 20° C. for 16 hours. The grey suspension obtained is diluted with distilled water (60 cc) and filtered. The orange-colored filtrate is treated with caustic soda (d=1.33) to pH 13 and extracted with ethyl acetate (200 cc). The organic phase is washed successively with distilled water (2×50 cc) and with saturated aqueous sodium chloride solution (50 cc) and dried over magnesium sulphate in the presence of charcoal 3S. After filtration, the yellow filtrate is concentrated to dryness under reduced pressure (30 mm Hg; 4 kPa) at 40° C. and an orange-colored oil (1.55 g) is thereby obtained. This product is purified by chromatography on a column (height: 25 cm; diameter: 2.6 cm) of silica gel (0.04–0.063 mm) under a slight excess pressure of nitrogen (40 kPa), eluting with ethyl acetate (750 cc) and then with a mixture (1500 cc) of ethyl acetate and methanol (90:10 by volume) and collecting 50-cc fractions. Fractions 12 to 44 are combined and concentrated to dryness under reduced pressure (30 mm Hg; 4 kPa) at 40° C. 10-(1-Diethylamino-2-propyl)-N-(3-methyl-1-butyl)-2-phenothiazinecarboxamide, L series (1.1 g), is obtained in the form of a yellow oil.

$[\alpha]_D^{20} = +15.6;$ (0.64%; chloroform).

10-(1-Diethylamino-2-propyl)-N-(3-methyl-1-butyl)-2-phenothiazinecarbothioamide, L series, may be prepared in the following manner:

3-Methylbutylamine (10.7 cc) is added to a solution of 10-(1-diethylamino-2-propyl)-2-phenothiazinecarbothioamide acid fumarate, L series (3 g), in absolute ethanol (45 cc) and this solution is saturated with hydrogen sulphide. The mixture is then brought to a temperature in the region of 105° C. for 16 hours and concentrated to dryness under reduced pressure (30 mm Hg; 4 pKa). The residual orange-colored oil is purified by chromatography on a column (height: 35 cm; diameter: 3 cm) of silica gel (0.2-0.063 mm), eluting with mixture (400 cc) of ethyl acetate and cyclohexane (70:30 by volume) and collecting 30-cc fractions. Fractions 7 to 11 are combined and concentrated to dryness under reduced pressure (30 mm Hg; 4 pKa) at 50° C. to give 10-(1-diethylamino-2-propyl)-N-(3-methyl-1-butyl)-2-phenothiazinecarbothioamide, L series (3.1 g), in the form of an orange-colored oil.

10-(1-Diethylamino-2-propyl)-2-phenothiazinecarbothioamide acid fumarate, L series, may be prepared in the following manner:

A solution of 10-(1-diethylamino-2-propyl)-2-phenothiazinecarbonitrile, L series (5.2 g), and triethylamine (2.2 cc) in anhydrous pyridine (104 cc) is saturated with hydrogen sulphide at 20° C. for 1 hour with stirring and then stirred at 20° C. for 17 hours. The reaction mixture is purged with nitrogen for 1 hour, poured into distilled water (500 cc) and extracted with ethyl acetate (2×250 cc). The combined organic phases are washed successively with distilled water (3×100 cc) and with saturated aqueous sodium chloride solution (100 cc), dried over magnesium sulphate and filtered. The yellow filtrate is concentrated to dryness under reduced pressure (30 mm Hg; 4 kPa) at 40° C. to give an orange-colored oil (6.5 g). This product is purified by chromatography on a column (height: 44 cm; diameter: 3.4 cm) of silica gel (0.2-0.063 mm), eluting with a mixture (3 liters of cyclohexane and ethyl acetate (30:70 by volume) and collecting 150-cc fractions. Fractions 8 to 17 are combined and concentrated to dryness under reduced pressure (30 mm Hg; 4 kPa) at 40° C., An orange-colored oil (5.08 g)

$([\alpha]_D^{20} = -33.7 \pm 0.6°;$ 1.006%; chloroform)

is obtained. This product is dissolved at a temperature in the region of 60° C. in ethanol (20 cc) and this solution is poured into a solution of fumaric acid (1.56 g) in ethanol (20 cc) at a temperature in the region of 60° C. and then left standing for 16 hours at a temperature in the region of 5° C. The crystals formed are drained, washed with ethanol (2×2 cc) and dried at 40° C. under reduced pressure (5 mm Hg; 0.7 kPa). 10-(1-Diethylamino-2-propyl)-2-phenothiazinecarbothiomide acid fumarate, L series (5.5 g) is thereby obtained in the form of yellow crystals, m.p. 186° C.

$[\alpha]_D^{20} = +29.1 \pm 0.6°$ (1%; dimethylformamide).

10-(1-Diethylamino-2-propyl)-2-phenothiazinecarbonitrile, L series, may be prepared in the following manner:

Sodium Carbonate (3.2 g) and iodoethane (2.3 cc) are added to a solution of 10-(1-ethylamino-2-propyl)-2-phenothiazinecarbonitrile, L series (7 g), in dimethylformamide (86 cc) and this mixture is then brought to a temperature in the region of 150° C. for 6 hours. After cooling, the reaction mixture is concentrated to dryness under reduced pressure (30 mm Hg; 4 kPa) at 40° and the residue is taken up with ethyl acetate (250 cc). The solution obtained is washed successively with distilled water (2×100 cc) and with saturated aqueous sodium chloride solution (100 cc), dried over magnesium sulphate in the presence of charcoal 3S and filtered. The yellow filtrate is concentrated to dryness under reduced pressure (30 mm Hg; 4 kPa) at 40° C. to give an orange-colored oil (6.65 g) which crystallizes slowly. This residue is dissolved in the minimum of isopropyl ether under reflux, the slight insoluble matter is filtered off while the mixture is hot and the filtrate is stored for 3 days at a temperature in the region of 5° C. The crystals formed are drained, washed with isopropyl ether (2×2 cc) and dried at 40° C. under reduced pressure (5 mm Hg; 0.7 kPa). 10-(1-Diethylamino-2-propyl)-2-phenothiazinecarbonitile, L series (2.9 g), is thereby obtained in the form of beige crystals, m.p. 83° C.

$[\alpha]_D^{20} = +9 \pm 0.3°;$ (0.978%; chloroform).

The filtrate is then concentrated to dryness under reduced pressure (30 mm Hg; 4 kPa) at 40° C. to give a further portion (2.3 g) of 10-(1-diethylamino-2-propyl)-2-phenothiazinecarbonitrile, L series, in the form of a beige solid, m.p. 81°-82° C.

$[\alpha]_D^{20} = +8.7 \pm 0.3°$ (1.2%; chloroform).

10-(1-Ethylamino-2-propyl)-2-phenothiazinecarbonitrile, L series, may be prepared in the following manner:

Ethylamine (30 cc) is added to a solution of 2-(2-cyano-10-phenothiazinyl)-1-propyl methanesulphonate, L series (16 g), in toluene (160 cc) and this mixture is brought to a temperature in the region of 105° C. for 24 hours. After cooling, the reaction mixture is concentrated to dryness under reduced pressure (30 mm Hg; 4 kPa) at 40° C. and the residue is taken up with ethyl ether (250 cc) and N aqueous sodium hydroxide solution (50 cc). After stirring, the organic phase is separated, washed successively with distilled water (50 cc) and with saturated aqueous sodium chloride solution (50 cc), dried over magnesium sulphate, filtered and concentrated to dryness under reduced pressure 30 mm Hg; 4 kPa) to give a yellow oil (13.8 g). This residue is dissolved at a temperature in the region of 60° C. in ethanol (46 cc), and this solution is poured into a solution at 60° C. of fumaric acid (5.2 g) in ethanol (46 cc) and then left for 16 hours at a temperature in the region of 5° C. The yellow precipitate formed is drained, washed with ethanol (2×5 cc) and dried at 40° C. under reduced pressure (5 mm Hg; 0.7 kPa). 10-(1-Ethylamino-2-propyl)-2-phenothiazinecarbonitrile fumarate, L series (9.7 g)

$([\alpha]_D^{20} = +6.2 \pm 0.4°; 1.008\%;$ dimethylformamide), is thereby obtained. this product is suspended in ethyl ether (200 cc) and N aqueous sodium hydroxide solution (100 cc) is added. After stirring, the organic phase is separated and the aqueous phase is extracted with ethyl ether (50 cc). The organic phases are combined, washed with saturated aqueous sodium chloride solution (100 cc), dried over magnesium sulphate, filtered and concentrated to dryness under reduced pressure (300 mm Hg; 40 kPa, then 30 mm Hg; 4 kPa) at 40° C. 10-(1-Ethylamino-2-propyl)-2-phenothiazinecarbonitrile, L series (7 g), is thereby obtained in the form of a yellow oil.

$[\alpha]_D^{20} = +12 \pm 0.3°$ (2% ;chloroform).

EXAMPLE 15

Using the procedure described in Example 12, starting with N-cyclopropylmethyl-10-[(2RS)-1-(1-pyrrolidinyl)-2-propyl]-2-phenothiazinecarboxamide (0.6 g), 1-[(2RS)-2-(2-cyclopropylmethylcarbamoyl-10-phenothiazinyl)propyl]-1-methylpyrrolidinium iodine (0.8 g) is obtained in the form of a pale yellow crystalline solid, m.p. about 150° C.

Proton NMR (250 MHz, DMSO-d$_6$, δ in ppm, J in Hz).

0.25 (2 Mt, 4H, cyclopropyl —CH$_2$—); 1.04 (Mt, 1H, cyclopropyl —CH—); 1.9 (d, J=6.5, 3H, —CH$_3$); 2 (Mt, 4H, pyrrolidine —CH$_2$—); 3 (S, 3H, →⊕NCH$_3$); 3.17 (DD, J=6 and 5.5, 2H, —CO—NH—CH$_2$—); 3.3 and 3.6 (2Mt, 1H and 3H respectively, pyrrolidine→⊕N—CH$_2$—); 3.76 (DD, J=14 and 1.5, 1H, 1H of →⊕N—CH$_2$); 4.11 (DD, J=14 and 9, 1H, 1H of →⊕N—CH$_2$—); 4.82 (Mt, J=9, 6.5 and 1.5, 1H, N—CH); 7 to 7.4 (Mt, 5H 5H aromatic); 7.58 (D, J=8, 1H, —H at 3-position); 7.59 (S, 1H, H at 1-position); 8.63 (T, J=5.5, 1H, —CONH—).

Infrared spectrum (KBr), characteristic bands in cm$^{-1}$: 3280, 2920, 1645, 1590, 1560, 1530, 1460, 870, 830, 755.

Thionyl chloride (5 cc) is added in the course of 5 minutes with stirring and at a temperature in the region of 4° C. to a suspension of 10-[(2RS)-1-(1-pyrrolidinyl)-2-propyl]-2-phenothiazinecarboxylic acid hydrochloride (3.5 g) in dichloromethane (100 cc), and stirring is continued for 90 minutes at a temperature of 20° C. The clear yellow solution obtained is concentrated to dryness under reduced pressure (30 mm Hg; 4 kPa) at 40° C. and dried to constant weight under reduced pressure (5 mm Hg; 0.67 kPa) at 50° C. The pasty yellow residue is dissolved in dry dichloromethane (40 cc) and cyclopropylmethylamine (3.8 g) is added dropwise at a temperature of 10° C. and with stirring.

Stirring is continued for 15 minutes at 10° C. and 16 hours at 20° C. The reaction mixture is washed with distilled water (3×3 cc) and the organic phase is dried over magnesium sulphate, filtered and concentrated to dryness under reduced pressure (30 mm Hg; 4 kPa) at 40° C. The residue is purified by chromatography on a column (height: 28 cm; diameter: 1.8 cm) of silica gel (0.06–0.2 mm), eluting with ethyl acetate (1 liter and collecting 80-cc fractions. Fractions 4 to 10 are combined and concentrated to dryness under reduced pressure (30 mm Hg; 4 kPa) at 40° C. to give N-cyclopropylmethyl-10-[(2RS)-1-(1-pyrrolidinyl)-2-propyl]-2-phenothiazinecarboxamide (3 g) in the form of a cream-colored meringue-like product.

10-[(2RS)-1-(1-Pyrrolidinyl)-2-propyl]-2-phenothiazinecarboxylic acid hydrochloride may be prepared in the following manner:

10-[(2RS)-1-(1-Pyrrolidinyl)-2-propyl]-2-phenothiazinecarbonitrile hydrochloride (3.72 g) is added to a solution of potassium hydroxide (1.7 g) in glycol (20 cc), and the mixture is stirred for 5 hours under reflux. After cooling, the yellow solution obtained is treated with a 3N solution (10 cc) of ethereal hydrogen chloride and diluted with acetone (100 cc) and ethyl ether (100 cc), then filtered. After seeding, the yellow filtrate allows the crystallization of a product which is drained, washed with ethyl ether (2×10 cc) and dried under reduced pressure (5 mm Hg; 0.68 kPa) at 40° C. 10-[(2RS)-1-(1-pyrrolidinyl)-2-propyl]-2-phenothiazinecarboxylic acid hydrochloride (3.5 g) is thereby obtained in the form of yellow crystals, m.p. 215°–217° C.

EXAMPLE 16

Using the procedure described in Example 12, starting with N-cyclobutylmethyl-10-[(2RS)-1-(1-pyrrolidinyl)-2-propyl]-2-phenothiazinecarboxamide (0.9 g), 1-[(2RS)-2-(2-cyclobutylethylcarbamoyl-10-phenothiazinyl)propyl]-1-methylpyrrolidinium iodide (0.9 g) is obtained in the form of a white crystalline solid, m.p. 140° C.

Proton NMR (250 MHz, DMSO-d$_6$, α in ppm, J in Hz).

1.65 to 2 (Mt, cyclobutyl —CH$_2$—); 1.91 (J=6.5, 3H—CH$_3$); 2.02 (Mt, 4H, pyrrolidine —CH$_2$—); 2.56 (Mt partially masked, cyclobutyl —CH—); 3 (S, 3H, →⊕NCH$_3$); 3.31 (Mt, 2H —CONH—CH$_2$—); 3.78 (broad D, J=14 and 1H, 1H of →⊕N—CH$_2$—); 4.10 (DD, J=14 and 9, 1H, 1H of→⊕N—CH$_2$—); 4.82 (Mt, J=9, 6.5 and approximately 1, 1H, N-CH); 7.05 to 7.4 (Mt, aromatic); 7.55 (D, J=8, 1H, -H at 3-position); 7.57 (S, 1H, H at 1-position); 8.51 (T, J=5.5, 1H, —CONH—).

Infrared spectrum (KBr), characteristic bands in cm$^{-1}$: 3280, 2970, 2860, 1650, 1590, 1560, 1525, 1460, 870, 830, 755.

N-Cyclobutylmethyl-10-[(2RS)-1-(1-pyrrolidinyl)-2-propyl]-2-phenothiazinecarboxamide may be prepared in the following manner:

Using a procedure similar to that described in Example 15, but starting with 10-[(2RS)-1-(1-pyrrolidinyl)-2-propyl]-2-phenothiazinecarboxylic acid hydrochloride (3.4 g) in dichloromethane (100 cc) and cyclobutylmethylamine (4.5 g), and after recrystallization in isopropyl ether, N-cyclobutylmethyl-10-[(1-pyrrolidinyl)-2-propyl]-2-phenothiazinecarboxamide (1.7 g) is obtained in the form of white crystals, m.p. 133° C.

EXAMPLE 17

Using the procedure described in Example 2, starting with N-cyclobutylmethyl-10-[1-(1-pyrrolidinyl)-2-propyl]-2-phenothiazinecarboxamide, L series (0.44 g), with dimethyl sulphate (0.13 g) in acetone (6 cc), 1-[2-(2-cyclobutylmethylcarbamoyl-10-phenothiazinyl)-propyl]-1-methylpyrrolidinium methysulphate, L series (0.39 g), is obtained in the form of a hygroscopic cream-colored powder, m.p. about 100° C.

$[\alpha]_D^{20} = +19 \pm 0.5°$ (1.03%; methanol)

Proton NMR (400 MHz, DMSO-d$_6$, δ in ppm, J in Hz).

1.65 to 2.1 (Mt, 10H, cyclobutyl —CH₂— and pyrrolidine —CH₂—); 1.91 (D, J=6.5, 3H, —CH₃); 2.56 (Mt, partially masked, cyclobutyl CH—); 3.01 (S, 3H, →⊕NCH₃); 3.32 (Mt, 2H —CONH—CH₂—); 3.4 (S, partially masked, —SO₃CH₃); 3.35 and 3.60 (2 Mt, 1H and 3H respectively, pyrrolidine →⊕N—CH₂—); 3.78 (broad D, J=14 and 1H, 1H of →⊕N—CH₂—); 4.11 (DD, J=14 and 9, 1H, 1H of →⊕N—CH₂—); 4.83 (Mt, J=9, 6.5 and approximately 1, 1H, N—CH); 7.05 to 7.45 (Mt, 5H aromatic); 7.54 (D, J=8, 1H, —H at 3-position); 7.58 (S, 1H, H at 1-position); 8.55 (T, J=5.5, 1H, —CONH—).

Infrared spectrum (KBr), characteristic bands in cm⁻¹: 2970, 2940, 2860, 1640, 1590, 1555, 1540, 1460, 1230, 1060, 1010, 875, 830, 745.

N-Cyclobutylmethyl-10-[1-(1-pyrrolidinyl)-2-propyl]-2-phenothiazinecarboxamide, L series, may be prepared in the following manner:

A lukewarm solution of mercuric acetate (3.19 g) in acetic acid (40 cc) is added to a solution of N-cyclobutylmethyl-10-[1-(1-pyrrolidinyl)-2-propyl]-2-phenothiazinecarbothioamide, L series (4.36 g), in acetic acid (20 cc). After stirring at a temperature in the region of 20° C. for 2 hours, the reaction mixture is filtered and the filtrate is concentrated to dryness under reduced pressure (30 mm Hg; 4 kPa) at 40° C. The residue is taken up with ethyl acetate (100 cc) and washed successively with 4N aqueous sodium hydroxide solution (2×50 cc) and then with distilled water (3×50 cc). The organic phase is dried over magnesium suphate, filtered and concentrated to dryness under reduced pressure (30 mm Hg; 4 kPa) at 40° C. to give a light yellow honey-like product (2.65 g) which is purified by chromatography on a column (height: 38 cm; diameter: 2 cm) of silica gel (0.06-0.2 mm), eluting with ethyl acetate (900 cc) and collecting 60-cc fractions. Fractions 3 to 12 are combined and concentrated to dryness under reduced pressure (30 mm Hg; 4 kPa) to give N-cyclobutylmethyl-10-[1-(1-pyrrolidinyl)-2-propyl]-2-phenothaizinecarboxamide, L series (1.88 g).

$[\alpha]_D^{20} = +22 \pm 0.6°$ (c=1%; methanol)

EXAMPLE 18

Using the procedure described in Example 2, starting with N-allyl-10-[1-(1-pyrrolidinyl)-2-propyl]-2phenothiazinecarboxamide, L series (0.7 g), with mehtyl iodide (0.47 cc) in acetone (25 cc), 1-[2-(2-allylcarbamoyl-10-phenothiazinyl)propyl]-1-methylpyrrolidinium iodide, L series (0.63 g), is obtained in the form of a yellow solid, m.p. about 200° C.

$[\alpha]_D^{20} = +20.7 \pm 0.8°$ (c=0.73%; methanol).

Proton NMR (250 MHz, DMSO-d₆, δ in ppm, J in Hz).

1.93 (D, J=7, 3H, —CH₃); 2 (Mt, 4H, pyrrolidine —CH₂—); 3 (S, 3H, →⊕NCH₃); 3.38 and 3.58 (2 Mt, the 1st partially masked, 1H and 3H respectively, pyrrolidine →⊕N—CH₂—); 3.76 (DD, J=14 and approximately 1, 1H, 1H of →⊕N—CH₂—); 3.94 (Mt, 2H, —CONH—CH₂—); 4.12 (DD, J=14 and 9, 1H, the other H of →⊕N—CH₂—); 4.83 (Mt, J=9, 7 and approximately 1, 1H, N—CH); 5.17 (Mt, 2H, allyl=CH₂); 5.94 (Mt, 1H, allyl —CH=); 7.05 to 7.4 (Mt, 5H, aromatic); 7.59 (DD, J=8 and approximately 1), 1H, —H at 3-position); 7.6 (D, J=1, 1H, —H at 1-position); 8.75 (T, J=5.5, 1H, —CONH—).

Infrared spectrum (KBr), characteristic bands in cm⁻¹: 3310, 2975, 1650, 1590, 1555, 1525, 1460, 1005, 875, 820, 760.

N-Allyl-10-[1-(1-pyrrolidinyl)-2-propyl]-2-phenothiazinecarboxamide, L series, may be prepared in the following manner:

Thionyl chloride (7.7 cc) is introduced in the course of 5 minutes with stirring into a suspension of 10-[1-(1-pyrrolidinyl)-2-phenothizine-carboxylic acid hydrochloride, L series (6 g), in methylene chloride (190 cc) while the temperature is maintained in the vicinity of 5° C. Stirring is continued for 4 hours while heating to a temperature in the region of 20° C., and the yellow solution obtained is concentrated to dryness under reduced pressure (30 mm Hg; 4 kPa) at 40° C. The residue is dissolved in methylene chloride (110 cc) and treated with a solution of allylamine (2.9 cc) in methylene chloride (30 cc) with stirring while the temperature is maintained at 5° C., and stirring is then continued for 16 hours at 20° C. The reaction mixture is diluted with ethyl acetate (250 cc), filtered, washed successively with saturated aqueous sodium hydrogen carbonate solution (50 cc), and with saturated aqueous sodium chloride solution (50 cc), dried over magnesium sulphate, filtered and concentrated to dryness under reduced pressure (30 mm Hg; 4 kPa) at 49° C. The oily yellow product (4.7 g) is purified by chromatography on a column (height: 35 cm; diameter: 4 cm) of silica gel (0.04-0.06 mm) with a slight excess pressure of nitrogen (40.5 kPa), eluting with a mixture (2 liters) of ethyl acetate and ethanol (90:10 by volume) and collecting 60-cc fractions. Fractions 6 to 28 are combined and concentrated to dryness under reduced pressure (30 mm Hg; 4 kPa) at 40° C. to give N-allyl-10[1-(1-pyrrolidinyl)-2-propyl]-2-phenothiazinecarboxamide, L form (3.98 g), in the form of a yellow oil.

10-[1-(1-Pyrrolidinyl)-2-propyl]-2-phenothiazinecarboxylic acid hydrochloride, L series, may be obtained in the following manner:

10-[1-(1-Pyrrolidinyl)-2-propyl]-2-phenothiazinecarbonitrile hydrochloride, L series (5 g) is added to a solution of potassium hydroxide (1.75 g) in glycol (30 cc), and the mixture is stirred for 4 hours under reflux. After cooling, the yellow solution obtained is diluted with acetone (75 cc) and a 3N solution (5 cc) of hydrochloric acid in ethyl ether, filtered and diluted again with acetone (75 cc) and a 3N solution (5 cc) of hydrochloric acid in ethyl ether. After seeding, crystallization is allowed to take place for 15 hours at a temperature in the region of 5° C. The solid obtained is drained, washed with ethyl ether (10 cc) and dried under reduced pressure (5 mm Hg; 0.7 kPa) at 40° C. 10-[1-(1-Pyrrolidinyl)-2-propyl]-2-phenothiazinecarboxylic acid hydrochloride, L series (2.9 g), is thereby obtained in the form of a light yellow solid, m.p. 200°-210° C. (melts forming a paste).

EXAMPLE 19

A solution of N-allyl-10-[1-(2,5-dihydro-1-pyrrolyl)-2-propyl]-2-phenothiazinecarboxamide, L series (1.1 g), and methyl iodide (0.4 g) in acetone (10 cc) is stirred for 3 days at a temperature in the region of 20° C. and then concentrated to dryness under reduced pressure (30 mm Hg; 4 kPa) at 45° C. The residue is purified by chromatography on a column (height: 30 cm; diameter: 3 cm) of silica gel (0.04-0.063 mm) under a slight excess pressure of nitrogen (40 kPa), eluting successively with a mixture (300 cc) of ethyl acetate and methanol (90:10 by volume) and then with a mixture (500 cc) of ethyl acetate and methanol (80:20 by volume) and collecting 40-cc fractions. Fractions 5 to 15 are combined and concentrated to dryness under reduced pressure (30 mm Hg; 4 kPa) at 40° C. and the residue is taken up with stirring for 30 minutes in isopropyl ether (40 cc). The suspension is filtered and the solid is washed with isopropyl ether (2×5 cc), drained and dried under reduced pressure (5 mm Hg; 0.7 kPa) at 40° C. 1-[2-(2-Allylcarbamoyl-10-pheno-thiazinyl)propyl]-1-methyl-2,5-dihydropyrrolium iodide, L series (0.66 g), is thereby obtained in the form of a yellow powder, m.p. about 170° C.

$[\alpha]_D^{20} = +14.0 \pm 0.5°$ (1%; methanol).

Proton NMR (250 MHz, DMSO-$d_6$, δ in ppm, J in Hz).

1.93 (D, J=7, 3H, —CH$_3$); 3.15 (S, 3H, →⊕NCH$_3$); 3.93 and 4.27 (2 Mt, 1H and 3H respectively; pyrroline →⊕N—CH$_2$—); 3.94 (Mt, 2H, —CONH—CH$_2$—); 4.28 (Mt, 1H, 1H of →⊕N—CH$_2$—); 4.52 (broad D, J=14, 1H, the other H of →⊕N—CH$_2$—); 4.79 (Mt, 1H, N—CH); 5.15 (Mt, 2H, allyl=CH$_2$); 5.9 (Mt, 2H, pyrroline —CH=); 5.93 (Mt, 1H, allyl —CH=); 7.05 to 7.4 (Mt, 5H, aromatic); 7.58 (broad S, 1H, —H at 1-position); 7.6 (D, J=8, 1H, —H at 3- position); 8.75 (T, J=5.5, 1H, —CONH—).

Infrared spectrum (KBr), characteristic bands in cm$^{-1}$: 3300, 2975, 1640, 1595, 1560, 1530, 1460, 1000, 930, 870, 825, 760.

N-Allyl-[1-(2,5-dihydro-1-pyrrolyl)-2-propyl]-2-phenothiazinecarboxamide, L series, may be prepared in the following manner:

The procedure is as described in Example 17, but starting with N-allyl-10-[1-(2,5-dihydro-1-pyrrolyl)-2-propyl]-2-phenothiazinecarbothioamide, L series (1.49 g), in acetic acid (25 cc) and a solution of mercuric acetate (1.16 g) in acetic acid (25 cc). The yellow meringue-like residue (1.27 g) is purified by chromatography on a column (height: 23 cm; diameter: 2.6 cm) of silica gel (0.04–0.63 mm) under a slight excess pressure of nitrogen (40 kPa), eluting with ethyl acetate (1.5 liters) and collecting 25-cc fractions. Fractions 10 to 58 are combined and concentrated to dryness under reduced pressure (30 mm Hg; 4 kPa) at 40° C. to give N-allyl-10-[1-(2,5-dihydro-1-pyrrolyl)-2-propyl]-2-phenothiazine-carboxamide, L series (0.45 g), in the form of a yellow resin.

EXAMPLE 20

Using the procedure described in Example 2, starting with N-propargyl-10-[1-(1-pyrrolidinyl)-2-propyl]-2-phenothiazinecarboxamide, L series (0.7 g), with methyl iodide (0.49 cc) in acetone (25 cc), 1-methyl-1-[2-(2-propargylcarbamoyl-10-phenothiazinyl)propyl]-pyrrolidinium iodide, L series (0.88 g), is obtained in the form of a pale yellow solid, m.p. about 140°–150° C.

$[\alpha]_D^{20} = +20.5 \pm 0.6°$ (1.02%; methanol).

Proton NMR (250 MHz, DMSO-$d_6$, δ in ppm, J in Hz).

1.93 (D, J=7, 3H, —CH$_3$); 2.02 (Mt, 4H, pyrrolidine —CH$_2$—); 3 (S, 3H, →⊕NCH$_3$); 3.18 (T, J=1.5, 1H, CH); 3.38 and 3.60 (2 Mt, the 1st partially masked, 1H and 3H respectively, pyrrolidine →⊕N—CH$_2$—); 3.76 (broad D, J=14, 1H, 1H of →⊕N—CH$_2$—); 4.10 (DD, J=14 and 9, 1H, the other H of →⊕N—CH$_2$—); 4.1 (Mt, 2H, —CONH—CCH$_2$—); 4.84 (Mt, J=9, 7 and small, 1H, N—CH); 7.05 to 7.4 (Mt, 5H aromatic); 7.57 (Mt, 2H, —H at 3-position and —H at 1-position); 9.01 (T, J=5.5, 1H, —CONH—).

Infrared spectrum (KBr), characteristic bands in cm$^{-1}$: 3280, 3250, 2970, 2120, 1650, 1590, 1560, 1525, 1460, 870, 830, 760.

N-Propargyl-10-[1-(1-pyrrolidinyl)-2-propyl]-2-phenothiazinecarboxamide, L series, may be prepared in the following manner:

Thionyl chloride (7.7 cc) is introduced in the course of 5 minutes with stirring into a suspension of 10-[1-(1-pyrrolidinyl)-2-propyl]-2-phenothiazine-carboxylic acid hydrochloride, L series (6 g), in mehylene chloride (190 cc) while the temperature is maintained in the vicinity of 5° C. Stirring is continued for 16 hours at a temperature in the region of 20° C. and the yellow solution obtained is concentrated to dryness under reduced pressure (30 mm Hg; 4 kPa) at 40° C. The residue is dissolved in methylene chloride (130 cc) and treated with a solution of propargylamine (2.45 cc) in mehylene chloride (25 cc) with stirring and while the temperature is maintained at 5° C., and stirring is then continued for 4 hours at 20° C. The reaction mixture is diluted with ethyl acetate (200 cc), filtered, washed successively with saturated aqueous sodium hydrogen carbonate solution (50 cc), and with saturated aqueous sodium chloride solution (50 cc), dried over magnesium sulphate, filtered and concentrated to dryness under reduced pressure (30 mm Hg;, 4 kPa) at 49° C. The oily brown residue (5.32 g) is dissolved in diethyl ether (70 cc) under reflux. After cooling, the solid formed is filtered off, washed with diethyl ether (10 cc) and taken up with ethyl acetate (40 cc). The solution obtained is washed successively with distilled water (50 cc) and then with saturated aqueous sodium chloride solution (50 cc), dried over magnesium sulphate, filtered and concentrated to dryness under reduced pressure (30 mm Hg; 4 kPa) at 40° C. to give a brown meringue-like product (2.8 g). This product is taken up with diethyl ether (50 cc) and the suspension obtained is stirred for 2 hours at 20° C. The solid is filtered off, washed with diethyl ether (2×5 cc) and dried under reduced pressure (5 mm Hg; 0.67 kPa) at 40° C. to give N-propyl-10-[1-(1-pyrrolidinyl)-2-propyl]-2-phenothiazinecarboxamide, L series (1.42 g), in the form of an ochre solid, m.p. 130° C.

$[\alpha]_D^{20} = +24.8 \pm 0.6°$ (c=1%; methanol).

EXAMPLE 21

A suspension of N-benzyl-10-[1-(1-pyrrolidinyl)-2-propyl]-2-phenothiazinecarboxamide hydrochloride, L series (0.48 g), in ethyl acetate (10 cc) is treated with N aqueous sodium hydroxide solution (1.5 cc) and stirred, and settling is allowed to take place. The organic phase is separated and the aqueous phase is re-extracted with ethyl acetate (10 cc). The organic phases are combined, washed with saturated aqueous sodium chloride solution (5 cc), dried over magnesium sulphate, filtered and concentrated to dryness under reduced pressure (30 mm Hg; 4 kPa) at 40° C. The yellow meringue-like residue (0.44 g) is dissolved in dry dimethylformamide (5 cc). Methyl iodide (0.14 g) is added and the mixture is stirred for 16 hours at a temperature in the region of 20° C. The reaction solution is poured into isopropyl ether (50 cc) with stirring and the oil formed is separated after settling has taken place, dissolved in acetone (10 cc) and reprecipitated with isopropyl ether (50 cc). After 10 minutes' stirring, the oil solidifies and the solid thereby formed is filtered off, washed with isopropyl ether (2×5 cc), drained and dried under reduced pressure (5 mm Hg; 0.7 kPa) at 50° C. 1-[2-(2-Benzyl-carbamoyl-10-phenothiazinyl)propyl]-1-methylpyrrolidinium iodide, L series (0.37 g) is thereby obtained in the form of an amorphous white solid, m.p. about 160°–162° C.

$[\alpha]_D^{20} = +16.8 \pm 0.6°$ (1.16%; methanol).

Proton NRM (250 MHz, DMSO-$d_6$, $\delta$ in ppm, J in Hz).

1.91 (D, J=6.5, 3H, —CH$_3$); 2 (Mt, 4H, pyrrolidine —CH$_2$—); 3 (S, 3H, →⊕NCH$_3$); 3.30 and 3.60 (2 Mt, 1H and 3H respectively, pyrrolidine →⊕N—CH$_2$—); 3.77 (DD, J=14, 1H, 1H of →⊕N—CH$_2$—); 4.11 (DD, J=14 and 9, 1H of →⊕N—CH$_2$—); 4.52 (D, J=5.5, 2H, —CONH—CH$_2$—); 4.82 (Mt, J=9, 6.5 and 1.5, 1H, N—CH); 7.05 to 7.45 (Mt, 10H, aromatic); 7.63 (Mt, 2H, —H at 3-position and —H at 1-position); 9.12 (T, J=5.5, 1H, —CONH—).

Infrared spectrum (KBr), characteristic bands in cm$^{-1}$: 3280, 2970, 1650, 1595, 1560, 1530, 1460, 870, 820, 755, 730, 700.

N-Benzyl-10-[1-(1-pyrrolidinyl)-2-propyl]-2-phenothiazinecarboxamide hydrocholride, L series, may be prepared in the following manner:

A 7.7 solution (0.59 cc) of hydrochloric acid in ethanol is added dropwise in the course of 5 minutes to a solution of N-benzyl-10-[1-(1-pyrrolidinyl)-2-propyl]-2-phenothiazinecarboxamide, L series (2.0 g), in absolute ethanol (30 cc). The solution is concentrated to dryness under reduced pressure (30 mm Hg; 4 kPa) and the residue is suspended in ethyl ether (100 cc) and dried under reduced pressure (5 mm Hg; 0.7 kPa) at 40° C. to give N-benzyl-10-[1-(1-pyrrolidinyl)-2-propyl]-2-phenothiazinecarboxamide hydrochloride, L series (1.91 g), in the form of a white solid, m.p. 218° C.

$[\alpha]_D^{20} = -18.8$ (0.746%; methanol).

Mercuric acetate (2.20 g), dissolved in acetic acid (20 cc), is added in the course of 20 minutes to a solution of N-benzyl-10-[1-(1-pyrrolidinyl)-2-propyl]-2-phenothiazinecarbothioamide, L series (3.18 g), in acetic acid (30 cc), and the mixture obtained is stirred for one hour at a temperature in the region of 20° C. The black suspension obtained is filtered on sintered glass plugged with Celite and the yellow filtrate is concentrated under pressure (30 mm Hg; 4 kPa) at 40° C. The residue is taken up with ethyl acetate (100 cc) and the organic phase is washed successively with normal sodium hydroxide (2×20 cc) and distilled water (2×20 cc) and with aqueous sodium chloride solution (20 cc) and dried over magnesium sulphate. After filtration, the yellow filtrate is concentrated under reduced pressure (30 mm Hg; 4 kPa) at 40° C. and a crude yellow oil (2.90 g) is thereby obtained. This residue is purified by chromatography on a column (height: 17 cm; diameter: 3.6 cm) of silica gel (0.04-0.06 mm) with a slight excess pressure of nitrogen (40.5 kPa), eluting with pure ethyl acetate (1.2 liters) and collecting 60-cc fractions. Fractions 8 to 17 are combined and are concentrated under reduced pressure (30 mm Hg; 4 kPa) at 40° C. to give n-benzyl-10-[1-(1-pyrrolidinyl)-2-propyl]-2-phenothiazinecarbothioamide, L series (2.3 g), in the form of a light brown resin.

A mixture of 10-[1-(1-pyrrolidinyl)-2-propyl]-2-phenothiazinecarbothioamide, L series (4.07 g), and benzylamine (6.0 cc) in ethanol (44 cc) is saturated with hydrogen sulphide and then heated for 18 hours to 175° C. in an autoclave. After cooling, the solution is concentrated to dryness under reduced pressure (30 mm Hg; 4 kPa) at 40° C. The residue is diluted with ethyl acetate (100 cc) and the organic phase is washed with distilled water (4×50 cc), dried over magnesium sulphate and filtered. The filtrate is concentrated to dryness under reduced pressure (30 mm Hg; 4 kPa) to give an orange-colored oil which is purified by chromatography on a column of 0.04–0.6 mm silica (height: 44.3 cm; diameter: 3.0 cm) with a slight excess pressure of nitrogen (40.5 kPa), eluting with pure ethyl acetate (1 liter) and collecting 100-cc fractions. Fractions 2 to 6 are combined and concentrated to dryness under reduced pressure (30 mm Hg; 4 kPa) at 40° C. A yellow oil (3.68 g) is obtained, characterized as N-benzyl-10-[1-(1-pyrrolidinyl)-2-propyl]-2-phenothiazinecarbothioamide, L series.

$[\alpha]_D^{20} = +1.3$ (1.080%; chloroform).

EXAMPLE 22

Using the procedure described in Example 21, starting with N-(2-methylphenyl)methyl-10[1-(1-pyrrolidinyl)-2-propyl]-2-phenothiazinecarboxamide hydrochloride, L series (1.2 g), in acetone (40 cc), 1-methyl-1-{2-(2-methylphenyl)methylcarbamoyl-10-phenothiazinyl]propyl}pyrrolidinium iodide, L series (1.1 g), is obtained in the form of a yellow crystalline solid, m.p. about 130° C.

Proton NMR (250 MHz, DMSO-$d_6$, $\delta$ in ppm, J in Hz).

1.92 (D, J=6.5, 3H, —CH$_3$); 2.02 (Mt, 4H, pyrrolidine —CH$_2$—); 2.36 (S, 3H, 2-methylbenzyl —CH$_3$); 3.01 (S, 3H, →⊕NCH$_3$); 3.35 and 3.60 (2 Mt, 1H and 3H respectively, pyrroline →⊕N—CH$_2$—); 3.79 (broad D, J=14, 1H, 1H of →⊕N—CH$_2$—); 4.11 (DD, J=14 and 9, 1H, 1H of →⊕N—CH$_2$—); 4.49 (D, J=5.5, 2H, —CONH—CH$_2$—); 4.85 (Mt, J=9, 6.5 and approximately 0.5, 1H, N—CH); 7.05 to 7.4 (Mt, 9H, aromatic); 7.64 (D, J=8, 1H, —H at 3-position); 7.64 (S, 1H, —H at 1-position); 8.98 (T, J=5.5, 1H, —CONH—).

Infrared spectrum (KBr), characteristic bands in cm$^{-1}$: 3260, 2970, 1650, 1595, 1560, 1525, 1485, 1460, 865, 820, 750.

N-(2-Methylphenyl)methyl-10-[1-(1-pyrrolidinyl)-2-propyl[-2-phenothiazinecarboxamide hydrochloride, L series, may be prepared in the following manner:

A 3N solution (3 cc) of hydrochloric acid in isopropyl ether is added dropwise in the course of 5 minutes to a solution of N-(2-methylbenzyl)-10-[1-(1-pyrrolidinyl)-2-propyl]-2-phenothiazinecarboxamide, L series (3.2 g), in ethyl acetate (25 cc). The solution is concentrated to dryness at 50° C. under reduced pressure (30 mm Hg; 4 kPa) to give a solid, which is taken up in isopropyl ether (20 cc). It is then drained washed with isopropyl ether (3×5 cc) and dried under reduced pressure (5 mm Hg; 0.7 kPa) at 40° C. to give N-(2-methylbenzyl)-10-[1-(1-pyrrolidinyl)-2-propyl]-2-phenothiazinecarboxamide hydrochloride, L series (2.4 g), in the form of a yellow solid, m.p. approximately 125° C.

Fumaric acid (0.7 g) and mercuric acetate (2.5 g) are added in the course of 20 minutes to a solution of N-(2-methylbenzyl)-10[1-(1-pyrrolidinyl)-2-propyl]-2-phenothiazinecarbothioamide, L series (3.8 g) in acetic acid (30 cc), and the mixture obtained is stirred for 12 hours at a temperature in the region of 20° C. The black suspension obtained is filtered on sintered glass plugged with Celite and the yellow filtrate is concentrated under reduced pressure (30 mm Hg; 4 kPa) at 40° C. The residue is taken up with ethyl acetate (100 cc) and the organic phase is washed successively with normal sodium hydroxide (2×20 cc) and distilled water (2×20 cc) and with saturated aqueous sodium chloride solution (20 cc) and dried over magnesium sulphate. After filtration, the yellow filtrate is concentrated under reduced pressure (30 mm Hg; 4 kPa) at 40° C. and N-(2-methylbenzyl)-10-[1-(1-pyrrolidinyl)-2-propyl]-2-phenothiazinecarboxamide, L series (3.2 g), is thereby obtained in the form of a yellow oil, which is used subsequently without further treatment.

A mixture of 10-[1-(1-pyrrolidinyl)-2-propyl]-2-phenothiazinecarbothioamide, L series (3.7 g), and 2-methylbenzylamine (5 g) in ethanol (50 cc) is saturated with hydrogen sulphide gas and then heated for 13 hours to 110° C. in an autoclave. After cooling, the solution is concentrated to dryness under reduced pressure (30 mm Hg; 4 kPa) at 40° C. The residue is diluted with ethyl acetate (100 cc) and the organic phase is washed with distilled water (4×50 cc), dried over magnesium sulphate and filtered. The filtrate is concentrated to dryness at 40° C. under reduced pressure (30 mm Hg; 4 kPa) to give an orange-colored oil which is purified by chromatography on a column of 0.06–0.2 mm silica (height: 30 cm; diameter; 4.5 cm), eluting with a 30/70 (by volume) mixture (1.5 liters) of cyclohexane and ethyl acetate and collecting 60-cc fractions. Fractions 9 to 17 are combined and evaporated under reduced pressure (30 mm Hg; 4 kPa) at 40° C. A yellow oil (3.8 g) is obtained, characterized as N-(2-methylbenzyl)-10-[1-(1-pyrrolidinyl)-2-propyl]-2-phenothiazinecarboxamide, L series.

EXAMPLE 23

N-Methylpyrrolidine (2.6 cc) is added to a solution of (2RS)-2-[2-(N-propylcarbamoyl)-10-phenothiazinyl)-propyl methanesulphonate (2.1 g) in acetonitrile (40 cc). The mixture is brought to reflux for 120 hours. After cooling, the solution obtained is concentrated to dryness under reduced pressure (30 mm Hg; 4 kPa) at 40° C. to give an oily residue, which is taken up with diethyl ether (50 cc). After one hour's stirring at 20° C., the suspension is filtered and the solid is washed with diethyl ether (3×10 cc) and then dried at 20° C. under reduced pressure (5 mmHg; 0.7 kPa. 1-Methyl-1-{(2RS)-2-[2-(N-propylcarbamoyl)-10-phenothiazinyl]-propyl}pyrrolidinium methylsulphonate (2 g) is thereby obtained in the form of an orange-colored solid.

(2RS)-2-[2-(N-Propylcarbamoyl)-10-phenothiazinyl]-propyl methanesulphonate may be obtained in the following manner:

Triethylamine (60 cc) and then a solution of methanesulphonyl chloride (33 cc) in dry methylene chloride (100 cc) are added with stirring to a solution, cooled to a temperature in the region of 0° C., of 10-[(1RS)-2-hydroxy-1-methylethyl]-N-propyl-2-phenothiazinecarboxamide (85.6 g) in methylene chloride (1 liter). The mixture is stirred at a temperature in the region of 0° C. for 30 minutes and then washed successively with a half-saturated solution (500 cc) of sodium bicarbonate and then saturated aqueous sodium chloride solution (250 cc). The organic phase is separated after settling has taken place, dried over magnesium sulphate, filtered and concentrated to dryness under reduced pressure (30 mm Hg; 4 kPa) at 40° C. The oily residue is crystallized in a mixture (700 cc) of isopropyl ether and acetonitrile (80:20 by volume). After 16 hours' stirring at a temperature in the region of 16° C., the suspension is filtered and the solid is washed with a mixture (100 cc) of isopropyl ether and acetonitrile (90:10 by volume) and then dried under reduced pressure (5 mm Hg; 0.7 kPa) at 20° C. to give a beige solid (77 g), m.p. 132° C. A portion (2 g) of this product is recrystallized in acetonitrile (35 cc) to give (2RS)-2-[2-(N-propylcarbamoyl)-10-phenothiazinyl]propyl methanesulphonate (1.2 g) in the form of a white solid, m.p. 138° C.

A solution of mercuric acetate (159.3 g) in acetic acid (1000 cc) is added with stirring in the course of 13 minutes and at a temperature in the region of 40° C. to a solution of 10-[(1RS)-2-hydroxy-1-methylethyl]-N-propyl-2-phenothiazinecarbothioamide (179.3 g) in acetic acid (500 cc). Stirring is continued for 40 minutes and the insoluble matter is filtered off and washed with ethyl acetate (2×100 cc). The combined organic phases are concentrated to dryness under reduced pressure (30 mm Hg; 4 kPa) at 50° C. to give an oily residue, which is dissolved in ethyl acetate (2500 cc). The solution obtained is washed with 4N aqueous sodium hydroxide solution (1 liter), then with distilled water (2×500 cc) and with saturated aqueous sodium chloride solution (500 cc). The organic phase is dried over magnesium sulphate and filtered and the filtrate is concentrated to dryness under reduced pressure (30 mm Hg; 4 kPa) at 40° C. to give a yellow oil (135.5 g) which is purified by chromatography on a column (height: 77 cm; diameter: 8.6 cm) of silica (0.06–0.2 mm), eluting with mixtures of increasing polarity of cyclohexane and ethyl acetate in the proportions 70:30 (5000 cc), 60:40 (5000 cc), 50:50 (5000 cc) and 25:75 (15000 cc) and collecting 1000-cc fractions. Fractions 16 to 25 are combined and concentrated to dryness under reduced pressure (30 mm Hg; 4 kPa) at 40° C. to give 10-[(1RS)-2-hydroxy-1-methylethyl]-N-propyl-2-phenothiazinecarboxamide (109.8 g) in the form of a pale yellow oil.

A mixture of 10-[(1RS)-2-hydroxy-1-methylethyl]-2-phenothiazinecarbothioamide (158.2 g) and propylamine (147.8 g) in anhydrous ethanol (500 cc) is brought to a temperature in the region of 150° C. for 16 hours. The brown solution obtained is concentrated to dryness under reduced pressure (30 mm Hg; 4 kPa) at 40° C. to give a residue which is dissolved in ethyl acetate (1200 cc). The solution obtained is washed with distilled water (5×300 cc), dried over magnesium sulphate, filtered and concentrated to dryness under reduced pressure (30 mm Hg; 4 kPa) at 40° C. to give 10-[(2RS)-2-hydroxy-1-methylethyl]-N-propyl-2-phenothiazinecarbothioamide (179.3 g) in the form of a yellow oil.

Triethylamine (98.4 cc) is added to a solution of 10-[(1RS)-2-hydroxy-1-methylethyl]-2-phenothiazine-carbonitrile (197.7 g) in anhydrous pyridine (750 cc), and hydrogen sulphide is bubbled through for 6 hours 30 minutes at 25° C. while the mixture is kept stirred. The mixture is stirred for 16 hours at 25° C., then purged with a stream of nitrogen for 2 hours and poured into distilled water (3000 cc). The oil which forms is separated after settling has taken place, washed with distilled water (3×1000 cc) and dissolved in ethyl acetate (3000 cc). The solution obtained is washed with distilled water (7×1 liter), dried over magnesium sulphate, filtered and concentrated to dryness under reduced pressure (30 mm Hg; 4 kPa) at 40° C. to give a yellow crystalline mass (225 g). This product is recrystallized in ethanol (1350 cc) to give 10-[(1RS)-2-hydroxy-1-methylethyl]-2-phenothiazinecarbothioamide (158.4 g) in the form of yellow crystals, m.p. 152° C.

EXAMPLE 24

A "110 volumes" aqueous hydrogen peroxide solution (0.55 cc) is introduced with stirring during 10 minutes into a solution of 10-[1-methyl-1-(1-pyrrolidinyl)-2-propyl]-N-propyl-2-phenothiazinecarboxamide, L series (2 g) in ethanol (7.5 cc), and stirring is continued for 64 hours at a temperature in the region of 20° C. Decolorizing charcoal (0.5 g) is added and stirring is continued for 3 hours. The reaction mixture is filtered and the pale yellow solution obtained is concentrated to dryness under reduced pressure (30 mm Hg; 4 kPa) at 40° C. The residue is dissolved in ethyl acetate (50 cc) and the solution is treated with decolorizing charcoal (2 g), dried over magnesium sulphate, filtered and concentrated to dryness under reduced pressure (30 mm Hg; 4 kPa) at 40° C. The oily residue is purified by chromatography on a column (height: 30 cm; diameter: 2.6 cm) of silica gel (0.04–0.063 cm) under a slight excess pressure of nitrogen (142 kPa), eluting with mixtures of increasing polarity of ethyl acetate and ethanol (80:20 by volume, 1000 cc, then 20:80 by volume 1000 cc) and collecting 80-cc fractions. Fractions 11 to 18 are combined and concentrated to dryness under reduced pressure (30 mm Hg; 4 kPa) at 40° C. to give a pale yellow oily residue (1.4 g). This residue is dissolved in methylene chloride (50 cc) and the solution is treated with decolorizing charcoal (0.5 g), filtered and concentrated to dryness under reduced pressure (30 mm Hg; 4 kPa) at 35° C. The light gold meringue-like product thereby obtained is dissolved in ethyl acetate (20 cc) in the heated state. The crystals formed after cooling are drained, washed with cold ethyl acetate (2×5 cc) and dried under reduced pressure (5 mm Hg; 0.67 kPa) at 35° C. 10-[1-(1-Pyrrolidinyl N-oxide)-2-propyl]-N-propyl-2-phenothiazinecarboxamide, L series (1.1 g), is thereby obtained in the form of white crystals, m.p. 155°–156° C.

Proton NMR (250 MHz, DMSO-$d_6$, δ in ppm, J in Hz).

0.93 (T, J=7.5, 3H, propyl —CH$_3$); 1.57 (sextet, J=7.5, 2H, propyl —CH$_2$—); 1.74 (D, J=7, 3H, —CH$_3$); 1.85 and 2.19 (2 Comp, 2H each respectively, pyrrolidine —CH$_2$—); 3.10 to 3.45 (Mt, pyrrolidine →$_\oplus$N —CH$_2$— and —CONH—CH$_2$); 3.86 (DD, J=12.5 and 5, 1H, 1H of →$_\oplus$N—CH$_2$—); 4.07 (DD, J=12.5 and 4, 1H, the other H of →$_\oplus$N—CH$_2$—); 5.4 (Mt, J=7.5, 5 and 4, 1H, N—CH); 6.95 to 7.3 (Mt, 6H, aromatic); 7.48 (broad D, J=8, 1H, —H at 3-position); 8.42 (T, J=5.5, 1H, —CONH—); 8.72 (Comp, 1H, —OH of hydrate of the N-oxide).

Infrared spectrum (KBr), characteristic bands in cm$^{-1}$: 3290, 3060, 2960, 2925, 2870, 1645, 1615, 1595, 1555, 1465, 1415, 1380, 1315, 1235, 990, 940, 890, 845, 750.

The present invention also relates to pharmaceutical compositions consisting of a product of general formula (I), in free form or in the form of an addition salt with a pharmaceutically acceptable acid, optionally in combination with any other pharmaceutically compatible product, which can be inert or physiologically active. The medicinal products according to the invention may be used parenterally, orally or rectally.

The sterile compositions for parenteral administration, which can be, in particular, used in the form of perfusions, are preferably solutions, aqueous or nonaqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in an injectable sterile medium.

The compositions for rectal administration are suppositories or rectal capsules, which contain, apart from the active product, excipients such as cocoa butter, semi-synthetic glycerides or polyethylene glycols.

As solid compositions for oral administration, tablets, pills, powders or granules may be used. In these compositions, the active product according to the invention (optionally in combination with another pharmaceutically compatible product) is mixed with one or more inert adjuvants or diluents such as sucrose, lactose or starch. These compositions can also comprise substances other than diluents, e.g. a lubricant such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, e.g. wetting products, sweeteners or flavorings.

In human therapy, the products according to the invention are especially useful in the treatment of spasmodic and painful manifestations of the digestive, urinary and respiratory tracts, or in gynecology.

The doses depend on the effect sought and the treatment period. For an adult, they are generally between 0.25 and 1500 mg per day, taken in unit doses at intervals.

Generally speaking, the doctor will determine the dosage he considers most appropriate in accordance with the age and weight and all other factors characteristic of the subject to be treated.

The examples which follow, given without implied limitation, illustrate the compositions according to the invention.

EXAMPLE A

Tablets containing 25 mg of active product (base) and having the following composition are prepared according to the usual procedure:

1-Methyl-1-[2-(2-propylcarbamoyl-10-phenothiazinyl)propyl]pyrrolidinium

| | |
|---|---|
| chloride | 27.5 mg |

-continued

| Starch | 83 mg |
|---|---|
| Silica | 30 mg |
| Magnesium stearate | 3 mg |

EXAMPLE B

A solution for intravenous administration containing 25 mg/cc of active product (base) is prepared according to the usual procedure: 1-Methyl-1-[2-(2-propylcarbamoyl-10-phenothiazinyl)propyl]pyrrolidinium

| chloride | 2.75 g |
|---|---|
| Ascorbic acid | 0.100 g |
| Neutral sodium sulphite | 0.050 g |
| 1N sodium hydroxide (q.s. pH 4) | approximately 0.08 cc |
| NaCl (q.s. isotonicity) | approximately 0.650 g |
| Water for injections | q.s. 100 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the intended spirit and scope of the appended claims. The above references are hereby incorporated by reference.

We claim:

1. A phenothiazine derivative of the formula:

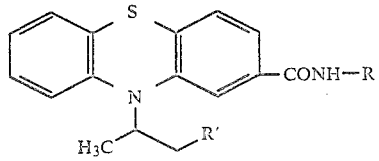

in which
the symbol R represents a 4- to 6-membered cycloalkyl radical or represents a radical —CH$_2$R'', in which R'' is a hydrogen atom, an alkyl radical containing 1 to 5 carbon atoms, an alkenyl or alkynyl radical containing 2 to 4 carbon atoms, a 3- to 6-membered cycloalkyl radical, a phenyl radical, optionally substituted with 1 or 2 halogen atoms or with a hydroxyl, alkyl, alkyloxy, trifluoromethyl or nitro radical, or a heterocyclic radical selected from furyl, thienyl or pyridyl, and
the symbol R' represents a radical of formula:

in which the symbols R$_1$ and R$_2$, which may be identical or different, represent alkyl, cycloalkyl, hydroxyalkyl or acetyloxyalkyl radicals, or, together with the nitrogen atom to which they are attached, form a pyrrolidinyl or piperidinyl group optionally substituted with 1 or 2 alkyl, hydroxyalkyl or acetyloxyalkyl radicals, and the symbol R$_3$ represents a phenethyl radical or an alkyl radical optionally substituted with a cycloalkyl radical containing 3 to 6 carbon atoms or substituted with a benzoyl radical,
the alkyl radicals being linear or branched and containing, except where otherwise stated, 1 to 4 carbon atoms, in the L form or in the form of a mixture of its isomeric forms.

2. A phenothiazine derivative according to claim 1, wherein
the symbol R represents a radical -CH$_2$R'' in which R'' is an alkyl radical containing 1 to 5 carbon atoms, an alkenyl or alkynyl radical containing 2 to 4 carbon atoms, a 3- to 6-membered cycloalkyl radical or a phenyl radical optionally substituted with an alkyl radical, and
the symbol R' represents: a radical of formula

in which the symbols R$_1$ and R$_2$, which may be identical or different, represent alkyl radicals or, together with the nitrogen atom to which they are attached, form a saturated or partially unsaturated pyrrolidinyl or piperidinyl group and the symbol R$_3$ represents a phenethyl radical or an alkyl radical optionally substituted with a cycloalkyl radical containing 3 to 6 carbon atoms or substituted with a benzoyl radical,
in the L form or in the form of a mixture of its isomeric forms.

3. A phenothiazine derivative according to claim 1, wherein
the symbol R represents a radical -CH$_2$R'' in which R'' is an alkyl radical containing 2 to 4 carbon atoms, an alkenyl radical containing 2 to 4 carbon atoms, a 3- or 4-membered cycloalkyl radical or a phenyl radical optionally substituted with an alkyl radical, and
the symbol R' represents: a radical of formula

in which the symbols R$_1$ and R$_2$, which may be identical or different, represent alkyl radicals or, together with the nitrogen atom to which they are attached, form a saturated pyrrolidinyl or piperidinyl group and the symbol R$_3$ represents a phenethyl radical or an alkyl radical optionally substituted with a cycloalkyl radical containing 3 to 6 carbon atoms,
in the L form or in the form of a mixture of its isomeric forms.

4. 1-Methyl-1-[2-(2-propylcarbamoyl-10-phenothiazinyl)propyl]pyrrolidinium, in its L form or in the form of a mixture of its isomeric forms.

5. 1-Phenethyl-1-[2-(2-propylcarbamoyl-10-phenothia-zinyl)propyl]pyrrolidinium, in its L form or in the form of a mixture of its isomeric forms.

6. 1-Methyl-1-{2-[2-(3-methylbutyl)carbamoyl-10-phenothiazinyl]propyl}pyrrolidinium, in its L form or in the form of a mixture of its isomeric forms.

7. 1-Methyl-1-{2-[2-(2-methylphenyl)methylcarbamoyl-10-phenothiazinyl]propyl}pyrrolidinium, in its L form or in the form of a mixture of its isomeric forms.

8. A pharmaceutical composition, comprising a pharmaceutically effective amount of at least one product according to claim 1, in the pure state or in combination with one or more compatible and pharmaceutically acceptable adjuvants or diluents.

* * * * *